(12) United States Patent
West

(10) Patent No.: US 11,638,813 B2
(45) Date of Patent: May 2, 2023

(54) IMPLANTABLE BLOOD PUMP ASSEMBLY INCLUDING ANTI-ROTATION MECHANISM FOR OUTFLOW CANNULA AND METHOD OF ASSEMBLING SAME

(71) Applicant: TC1 LLC, St. Paul, MN (US)

(72) Inventor: Dustin Seth West, Leominster, MA (US)

(73) Assignee: TC1 LLC, St. Paul, MN (US)

( * ) Notice: Subject to any disclaimer, the term of this patent is extended or adjusted under 35 U.S.C. 154(b) by 197 days.

(21) Appl. No.: 16/946,734

(22) Filed: Jul. 2, 2020

(65) Prior Publication Data
US 2021/0085845 A1 Mar. 25, 2021

Related U.S. Application Data

(60) Provisional application No. 62/904,950, filed on Sep. 24, 2019.

(51) Int. Cl.
| | | |
|---|---|---|
| *A61M 60/859* | (2021.01) | |
| *A61M 60/422* | (2021.01) | |
| *A61M 60/148* | (2021.01) | |
| *A61M 60/205* | (2021.01) | |

(52) U.S. Cl.
CPC ........ *A61M 60/422* (2021.01); *A61M 60/148* (2021.01); *A61M 60/205* (2021.01); *A61M 2205/8206* (2013.01)

(58) Field of Classification Search
CPC .............. A61M 60/857; A61M 60/205; A61M 1/3653; A61M 1/3659; A61M 1/3666; A61M 2205/04; A61M 2205/103
See application file for complete search history.

(56) References Cited

U.S. PATENT DOCUMENTS

| | | | |
|---|---|---|---|
| 6,123,659 A | * | 9/2000 | le Blanc ............. A61M 60/237 600/16 |
| 7,824,358 B2 | | 11/2010 | Cotter et al. |
| 2004/0087986 A1 | | 5/2004 | Ott |
| 2013/0225909 A1 | * | 8/2013 | Dormanen .......... A61M 60/232 600/16 |

(Continued)

OTHER PUBLICATIONS

International Search Report and Written Opinion for International Patent Application No. PCT/US2020/070228, dated Nov. 3, 2020, 14 pages.

*Primary Examiner* — Michael J D'Abreu
(74) *Attorney, Agent, or Firm* — Armstrong Teasdale LLP

(57) ABSTRACT

Disclosed herein is an implantable blood pump assembly that includes a housing defining an inlet, an outlet, and a flow path extending from the inlet to the outlet, a rotor positioned within the flow path, a stator positioned within the housing and operable to drive the rotor, and an outflow cannula. The outflow cannula includes a coupler assembly configured for removable mechanical connection to the outlet coupler, and includes a first component of an anti-rotation mechanism and a first component of an axial lock. The housing includes an outlet coupler that includes a second component of the anti-rotation mechanism and a second component of the axial lock. The first and second components of the anti-rotation mechanism are positioned to engage one another prior to the first and second components of the axial lock during insertion of the outflow cannula into the housing outlet.

20 Claims, 16 Drawing Sheets

(56) References Cited

U.S. PATENT DOCUMENTS

2013/0261375 A1* 10/2013 Callaway ............ A61M 60/871
                                                                             600/16
2016/0121033 A1    5/2016  Cotter et al.
2017/0232168 A1    8/2017  Reichenbach et al.

\* cited by examiner

IMPLANTABLE BLOOD PUMP ASSEMBLY INCLUDING ANTI-ROTATION MECHANISM FOR OUTFLOW CANNULA AND METHOD OF ASSEMBLING SAME

CROSS-REFERENCE TO RELATED APPLICATIONS

This application claims priority to U.S. provisional patent application Ser. No. 62/904,950, filed Sep. 24, 2019, the disclosure of which is hereby incorporated by reference in its entirety.

BACKGROUND OF THE DISCLOSURE a. Field of the Disclosure

The present disclosure relates generally to mechanical circulatory support systems, and more specifically relates to coupling mechanisms for connecting outflow cannulas to implantable blood pumps.

b. Background

Ventricular assist devices, known as VADs, are implantable blood pumps used for both short-term (i.e., days, months) and long-term (i.e., years or a lifetime) applications where a patient's heart is incapable of providing adequate circulation, commonly referred to as heart failure or congestive heart failure. A patient suffering from heart failure may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

In conventional VADs, an outflow cannula is connected to a pump housing to direct blood from the pump to a patient's ascending or descending aorta. In at least some known VADs, the outflow cannula is connected to the pump housing during the implant procedure. Further, at least some known VADs permit the outflow cannula to rotate relative to the pump housing after assembly (i.e., post-operatively). Additionally, some known VADs do not limit the amount of rotation of the outflow cannula relative to the pump housing during assembly. Consequently, known VADs may permit the outflow cannula to be subjected to excessive rotation and/or torsion during the implant procedure and/or post-operatively.

Accordingly, a need exists for improved coupling mechanisms for connecting outflow cannulas to implantable blood pumps.

SUMMARY OF THE DISCLOSURE

The present disclosure is directed to an implantable blood pump assembly that includes a housing defining an inlet, an outlet, and a flow path extending from the inlet to the outlet, a rotor positioned within the flow path and operable to pump blood from the inlet to the outlet, a stator positioned within the housing and operable to drive the rotor, and an outflow cannula. The outflow cannula includes a coupler assembly configured for removable mechanical connection to the outlet coupler, and includes a first component of an anti-rotation mechanism and a first component of an axial lock. The housing includes an outlet coupler that includes a second component of the anti-rotation mechanism and a second component of the axial lock. The first and second components of the anti-rotation mechanism are positioned to engage one another prior to the first and second components of the axial lock during insertion of the outflow cannula into the housing outlet.

The present disclosure is further directed to an implantable blood pump assembly that includes a housing defining an inlet, an outlet, and a flow path extending from the inlet to the outlet, a rotor positioned within the flow path and operable to pump blood from the inlet to the outlet, a stator positioned within the housing and operable to drive the rotor, and an outflow cannula. The outflow cannula includes a coupler assembly configured for removable mechanical connection to the outlet coupler, and includes an adapter sleeve and a screw ring rotatably coupled to the adapter sleeve. The adapter sleeve includes one of: (i) a plurality of longitudinally-extending grooves or (ii) a plurality of longitudinally-extending splines. The screw ring includes first threads. The housing includes an outlet coupler that includes the other of (i) the plurality of longitudinally-extending grooves and (ii) the plurality of longitudinally-extending splines, and second threads configured to threadably engage the first threads. The plurality of splines are configured for mating engagement with the plurality of grooves to inhibit relative rotation of the outflow cannula and the pump housing. The plurality of grooves and the plurality of splines are positioned to engage one another prior to the first and second threads during insertion of the outflow cannula into the housing outlet.

The present disclosure is further directed to a method of assembling an implantable blood pump. The method includes providing an outflow cannula including a coupler assembly that includes a first component of an anti-rotation mechanism and a first component of an axial lock. The method further includes providing a blood pump including a housing defining an inlet, an outlet, and a flow path extending from the inlet to the outlet, where the housing includes an outlet coupler that includes a second component of the anti-rotation mechanism and a second component of the axial lock. The method further includes aligning the first component of the anti-rotation mechanism with the second component of the anti-rotation mechanism, and inserting the outflow cannula into the housing outlet such that the first and second components of the anti-rotation mechanism engage one another prior to the first and second components of the axial lock. The anti-rotation mechanism limits rotation of the outflow cannula relative to the pump housing. The method further includes engaging the first component of the axial lock with the second component of the axial lock such that the axial lock inhibits axial movement of the outflow cannula relative to the pump housing.

DETAILED DESCRIPTION OF THE DISCLOSURE

The present disclosure is directed to implantable blood pump assemblies and, more specifically, to coupling mechanisms for connecting outflow cannulas to implantable blood pumps.

Figure 1:
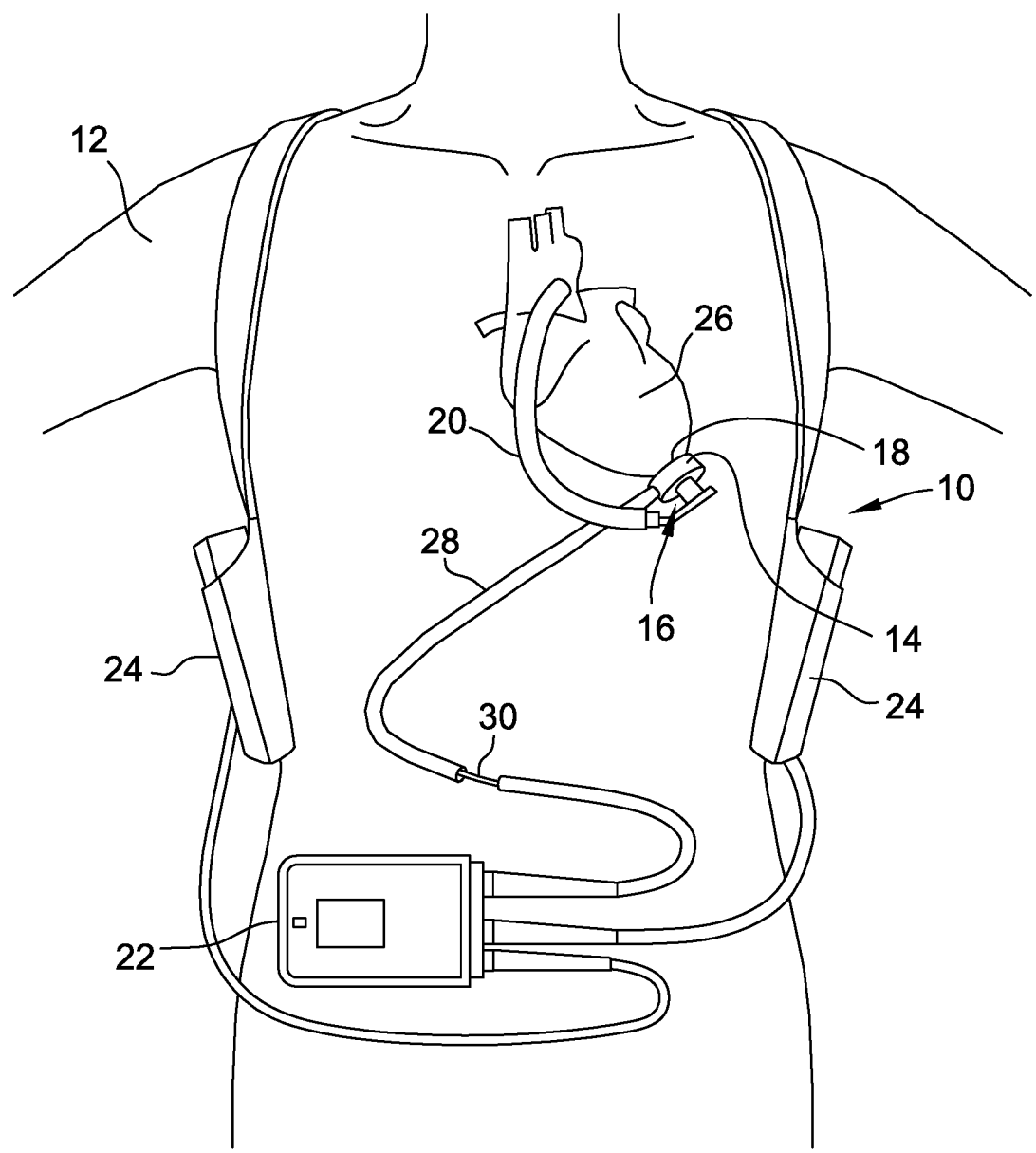
FIG. 1 is an illustration of a mechanical circulatory support system implanted in a patient's body.

Referring to the drawings, FIG. 1 is an illustration of a mechanical circulatory support system 10 implanted in a patient's body 12. The mechanical circulatory support system 10 includes an implantable blood pump assembly 14 that includes a blood pump 16, a ventricular cuff 18, and an outflow cannula 20. The mechanical circulatory support system 10 also includes an external system controller 22 and one or more power sources 24.

Figure 2:
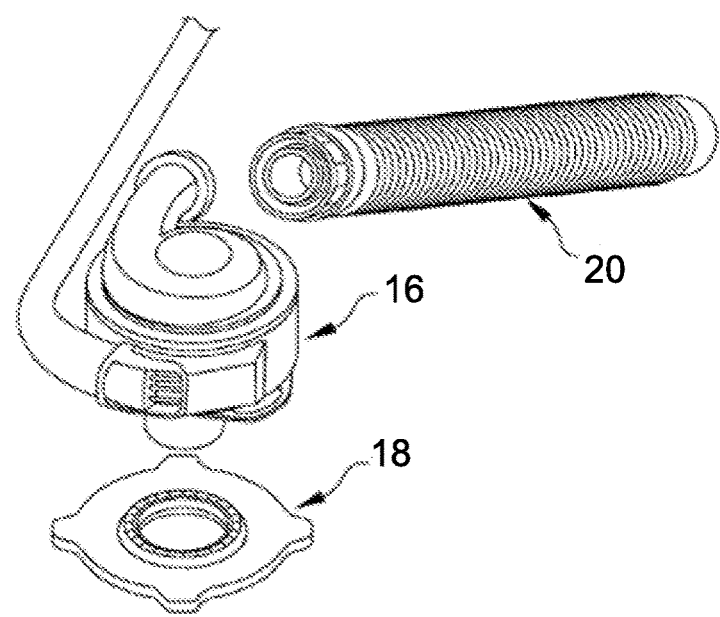
FIG. 2 is an exploded view of certain components of the circulatory support system shown in FIG. 1.

The blood pump assembly 14 can be implemented as or can include a ventricular assist device (VAD) that is attached to an apex of the left ventricle, as illustrated, or the right ventricle, or both ventricles of the heart 26. With additional reference to FIG. 2, the blood pump assembly 14 can be attached to the heart 26 via the ventricular cuff 18 which is sewn to the heart 26 and coupled to the blood pump assembly 14, as described further herein. The other end of the blood pump assembly 14 connects to the ascending or descending aorta via the outflow cannula 20 so that the blood pump assembly 14 effectively diverts blood from the weakened ventricle and propels it to the aorta for circulation to the rest of the patient's vascular system. The VAD can include a centrifugal (as shown) or axial flow pump as described in further detail herein that is capable of pumping the entire output delivered to the left ventricle from the pulmonary circulation (i.e., up to 10 liters per minute).

FIG. 1 illustrates the mechanical circulatory support system 10 during battery powered operation. A communication line 28 connects the implanted blood pump assembly 14 to the external system controller 22, which monitors system 10 operation. In the illustrated embodiment, the communication line 28 is shown as a driveline that exits through the patient's abdomen 30, although it should be understood that the blood pump assembly 14 may be connected to the external system controller 22 via any suitable communication line, including wired and/or wireless communication. The system can be powered by either one, two, or more batteries 24. It will be appreciated that although the system controller 22 and power source 24 are illustrated outside/external to the patient body, the communication line 28, system controller 22 and/or power source 24 can be partially or fully implantable within the patient, as separate components or integrated with the blood pump assembly 14.

Figure 3:
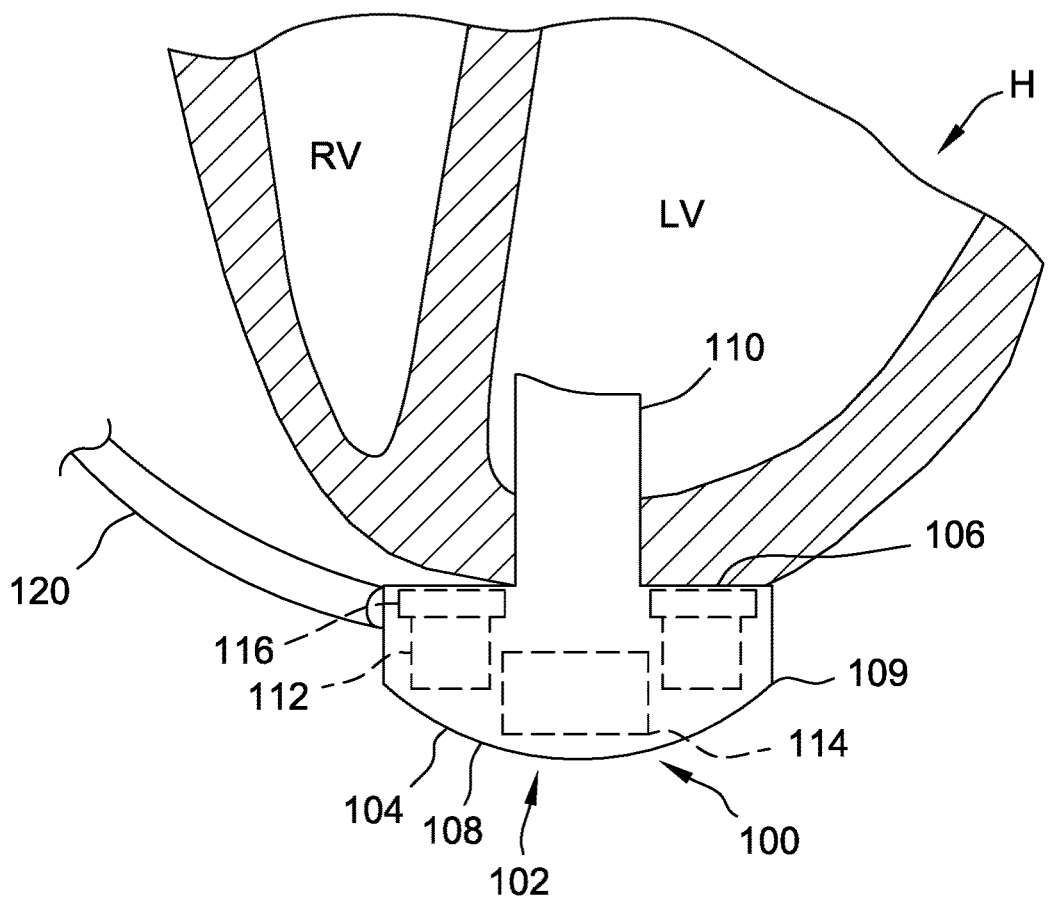
FIG. 3 is an illustration of a blood pump assembly suitable for use in the mechanical circulatory support system of FIG. 1, the blood pump assembly shown in an operational position implanted in a patient's body.
Figure 4:
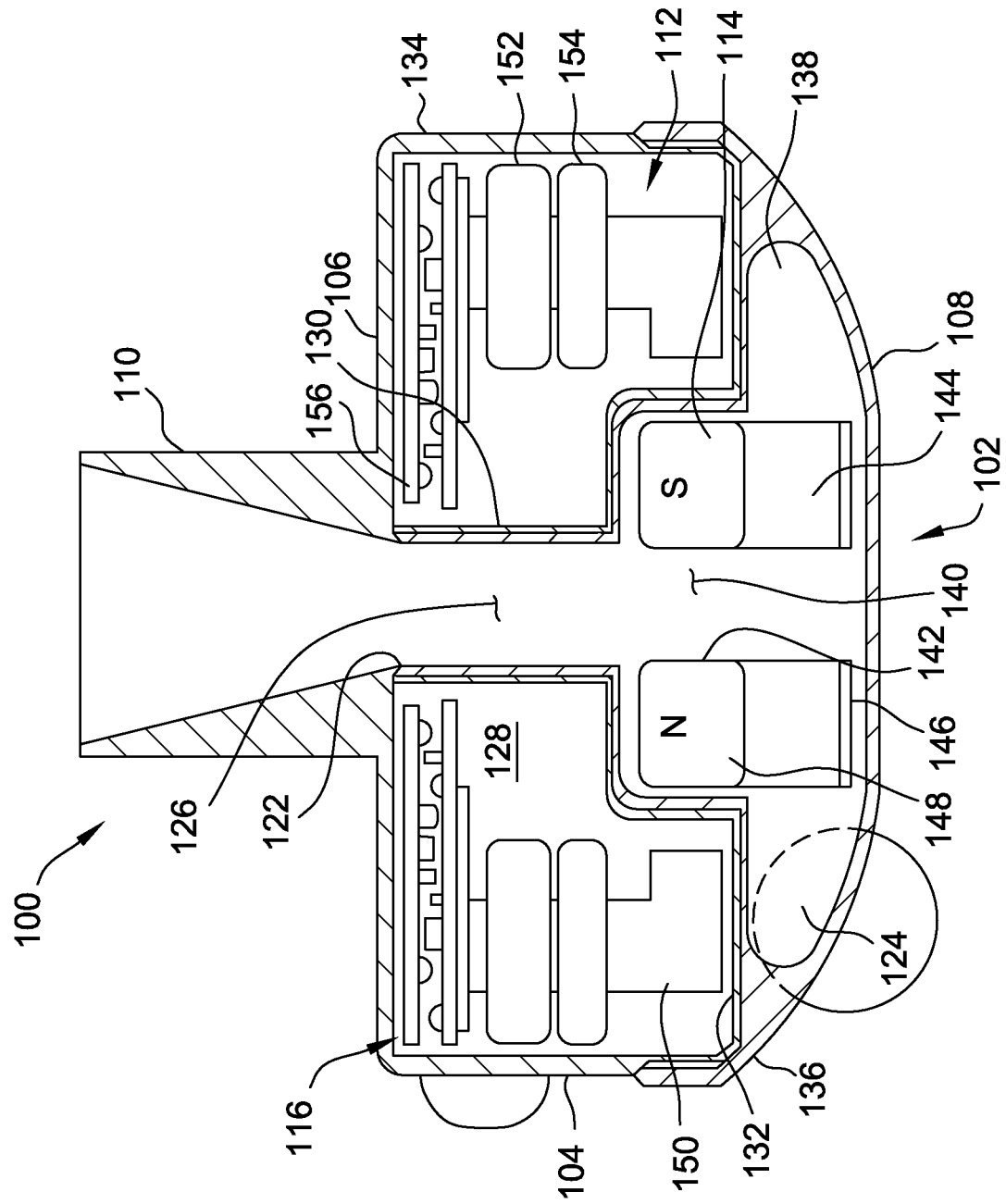
FIG. 4 is a schematic cross-sectional view of the blood pump assembly of FIG. 3.

FIG. 3 is an illustration of an implantable blood pump assembly 100 suitable for use in the mechanical circulatory support system 10 of FIG. 1, where the blood pump assembly 100 is shown in an operational position implanted in a patient's body. FIG. 4 is a schematic cross-sectional view of the blood pump assembly 100 of FIG. 3. In the illustrated embodiment, the blood pump assembly 100 is a left ventricular assist blood pump assembly connected to the left ventricle LV of the heart H.

The blood pump assembly 100 includes a blood pump 102 including a circular shaped housing 104 having a first outer face or wall 106 and a second outer face or wall 108. The blood pump assembly 100 further includes an inflow cannula 110 (generally, an inlet conduit) that, in the illustrated embodiment, extends from the first outer wall 106 of the pump housing 104. When the blood pump assembly 100 is implanted into a patient's body, as shown in FIG. 3, the first outer wall 106 of the housing 104 is positioned against the patient's heart H, and the second outer wall 108 of the housing 104 faces away from the heart H. The inflow cannula 110 extends into the left ventricle LV of the heart H to connect the blood pump assembly 100 to the heart H. The second outer wall 108 of the housing 104 has a chamfered edge 109 to avoid irritating other tissue that may come into contact with the blood pump assembly 100, such as the patient's diaphragm.

The blood pump assembly 100 further includes a stator 112, a rotor 114, and an on-board controller 116, all of which are enclosed within the pump housing 104. In the illustrated embodiment, the stator 112 and the on-board controller 116 are positioned on the inflow side of the pump housing 104 toward the first outer wall 106, and the rotor 114 is positioned along the second outer wall 108. In other embodiments, the stator 112, the rotor 114, and the on-board controller 116 may be positioned at any suitable location within the pump housing 104 that enables the blood pump assembly 100 to function as described herein. Power is supplied to operational components of the blood pump assembly 100 (e.g., the stator 112 and the on-board controller 116) from a remote power supply via a power supply cable 120.

With additional reference to FIG. 4, the pump housing 104 defines an inlet 122 for receiving blood from a ventricle of a heart (e.g., left ventricle LV), an outlet 124 for returning blood to a circulatory system, and a flow path 126 extending from the inlet 122 to the outlet 124. The pump housing 104 further defines an internal compartment 128 separated from the flow path 126, for example, by one or more dividing walls 130. The pump housing 104 also includes an intermediate wall 132 located between the first outer wall 106 and the second outer wall 108, and a peripheral wall 134 that extends between the first outer wall 106 and the intermediate wall 132. Together, the first outer wall 106, the dividing wall 130, the intermediate wall 132, and the peripheral wall 134 define the internal compartment 128 in which the stator 112 and the on-board controller 116 are enclosed.

In the illustrated embodiment, the pump housing 104 also includes a cap 136 removably attached to the pump housing 104 along the intermediate wall 132. The cap 136 is threadably connected to the pump housing 104 in the illustrated embodiment, although in other embodiments the cap 136 may be connected to the pump housing 104 using any suitable connection means that enables the blood pump assembly 100 to function as described herein. In some embodiments, for example, the cap 136 is non-removably connected to the pump housing 104, for example, by welding. The removable cap 136 includes the second outer wall 108, the chamfered edge 109, and defines the outlet 124. The cap 136 also defines a volute 138 that is in fluid communication with the outlet 124, and a rotor chamber 140 in which the rotor 114 is positioned. The cap 136 can be attached to the pump housing 104 using any suitable connection structure. For example, the cap 136 can be engaged via threads with the peripheral wall 134 to seal the cap 136 in engagement with the peripheral wall 134.

The rotor 114 is positioned within the blood flow path 126, specifically, within the rotor chamber 140, and is operable to rotate in response to an electromagnetic field generated by the stator 112 to pump blood from the inlet 122 to the outlet 124. The rotor defines a central aperture 142 through which blood flows during operation of the blood pump 102. The rotor 114 includes impeller blades 144 located within the volute 138 of the blood flow path 126, and a shroud 146 that covers the ends of the impeller blades 144 facing the second outer wall 108 to assist in directing blood flow into the volute 138.

In the illustrated embodiment, the rotor 114 includes a permanent magnet 148 that defines the central aperture 142. The permanent magnet 148 has a permanent magnetic north pole N and a permanent magnetic south pole S for combined active and passive magnetic levitation of the rotor 114 and for rotation of the rotor 114. In operation, the stator 112 is controlled to drive (i.e., rotate) the rotor and to radially levitate the rotor 114 by generating electromagnetic fields that interact with the permanent magnetic poles S and N of the permanent magnet 148.

Any suitable stator 112 can be employed to rotate the rotor 114. The stator 112 generally includes a plurality of winding structures that generate suitable electromagnetic fields that interact with the rotor 114 to cause rotor 114 to rotate and levitate. In the illustrated embodiment, the stator 112 includes a plurality of pole pieces 150 arranged circumferentially at intervals around the dividing wall 130. The example blood pump assembly 100 includes six pole pieces 150, two of which are visible in FIG. 4. In other embodiments, the blood pump assembly 100 can include more than or less than six pole pieces, such as four pole pieces, eight pole pieces, or any other suitable number of pole pieces that enables the blood pump assembly 100 to function as described herein. In the illustrated embodiment, each of the pole pieces 150 includes a drive coil 152 for generating an electromagnetic field to rotate the rotor 114, and a levitation coil 154 for generating an electromagnetic field to control the radial position of the rotor 114.

Suitable methods for controlling the stator 112 and generating electromagnetic fields to rotate and radially levitate the rotor 114 are described, for example, in U.S. Pat. No. 9,849,224, the entire contents of which are incorporated herein by reference for all purposes. Although the drive coil 152 and levitation coil 154 are shown as separate coils in the illustrated embodiment, it should be understood that the drive coil 152 and levitation coil 154 may be implemented as a single coil configured to generate electromagnetic fields for both rotating and radially levitating the rotor 114.

The inflow cannula 110 is attached to the pump housing 104 at the inlet 122. The pump housing 104 includes suitable connecting structure at the inlet 122 for connecting the inflow cannula 110 to the pump housing 104. In some embodiments, for example, the pump housing 104 includes a threaded sleeve that threadably engages threads on a downstream or proximal end of the inflow cannula 110 to connect the inflow cannula 110 to the pump housing 104.

The on-board controller 116 is operatively connected to the stator 112, and is configured to control operation of the pump 102 by controlling the supply of electrical current to the stator 112 and thereby control rotation of the rotor 114. In some embodiments, the on-board controller 116 is configured to perform closed-loop speed control of the pump rotor 114 based on feedback received from one or more sensors (e.g., pressure sensors, flow sensors, accelerometers, etc.) included within the blood pump assembly 100. The on-board controller 116 can be configured to control the rotor 114 in continuous flow operation and/or pulsatile flow operation.

The on-board controller 116 can include one or more modules or devices that are enclosed within pump housing 104. The on-board controller 116 can generally include any suitable computer and/or other processing unit, including any suitable combination of computers, processing units and/or the like that may be communicatively coupled to one another (e.g., on-board controller 116 can form all or part of a controller network). Thus, on-board controller 116 can include one or more processor(s) and associated memory device(s) configured to perform a variety of computer-implemented functions (e.g., performing the methods, steps, calculations and/or the like disclosed herein). As used herein, the term "processor" refers not only to integrated circuits referred to in the art as being included in a computer, but also refers to a controller, a microcontroller, a micro-computer, a programmable logic controller (PLC), an application specific integrated circuit (ASIC), a digital signal processor (DSP), a field programmable gate array (FPGA), and other programmable circuits. Additionally, the memory device(s) of on-board controller 116 may generally include memory element(s) including, but not limited to, non-transitory computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) can generally be configured to store suitable computer-readable instructions that, when implemented by the processor(s), configure the on-board controller 116 to perform various functions including, but not limited to, controlling the supply of electrical current to the stator 112, adjusting the speed of the rotor 114, and various other suitable computer-implemented functions.

In the illustrated embodiment, the on-board controller 116 is implemented as one or more circuit boards 156 and various components carried on the circuit boards (e.g., processors and memory devices) to control operation of the pump 102 by controlling the electrical supply to the stator 112.

A communication line (e.g., communication line 28) couples the blood pump assembly 100 and on-board controller 116 to the external system controller 22, which monitors system operation via various software applications. The blood pump assembly 100 itself may also include several software applications that are executable by the on-board controller 116 for various functions, such as to control radial levitation and/or drive of the rotor 114 of the pump assembly 100 during operation. The external system controller 22 can in turn be coupled to batteries 24 or a power module (not shown) that connects to an AC electrical outlet. The external system controller 22 can also include an emergency backup battery (EBB) to power the system (e.g., when the batteries 24 are depleted) and a membrane overlay, including Bluetooth capabilities for wireless data communication. An external computer that is configurable by an operator, such as clinician or patient, can further be coupled to the circulatory support system 10 for configuring the external system controller 22, the implanted blood pump assembly 100, and/or patient specific parameters, updating software on the external system controller 22 and/or the implanted blood pump assembly 100, monitoring system operation, and/or as a conduit for system inputs or outputs.

Figure 5:
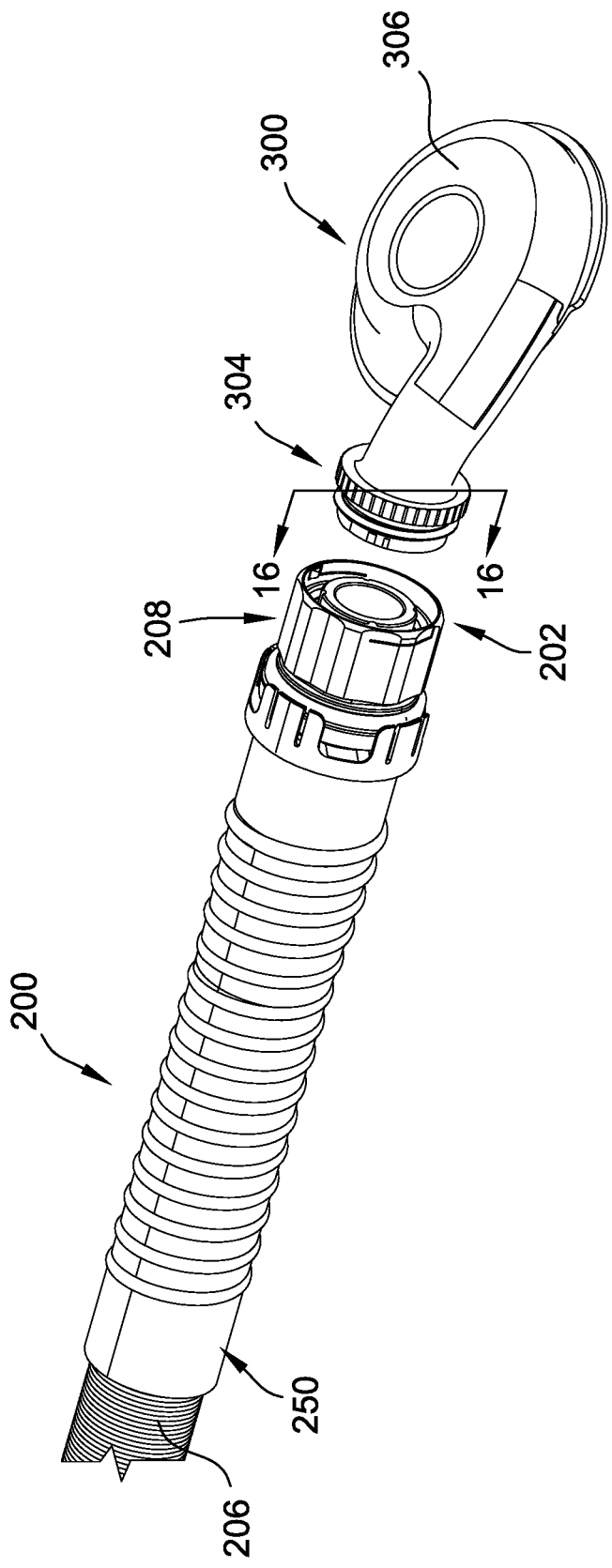
FIG. 5 is a perspective view of an outflow cannula and a portion of a pump housing suitable for use in the blood pump assembly of FIGS. 3 and 4.
Figure 6:
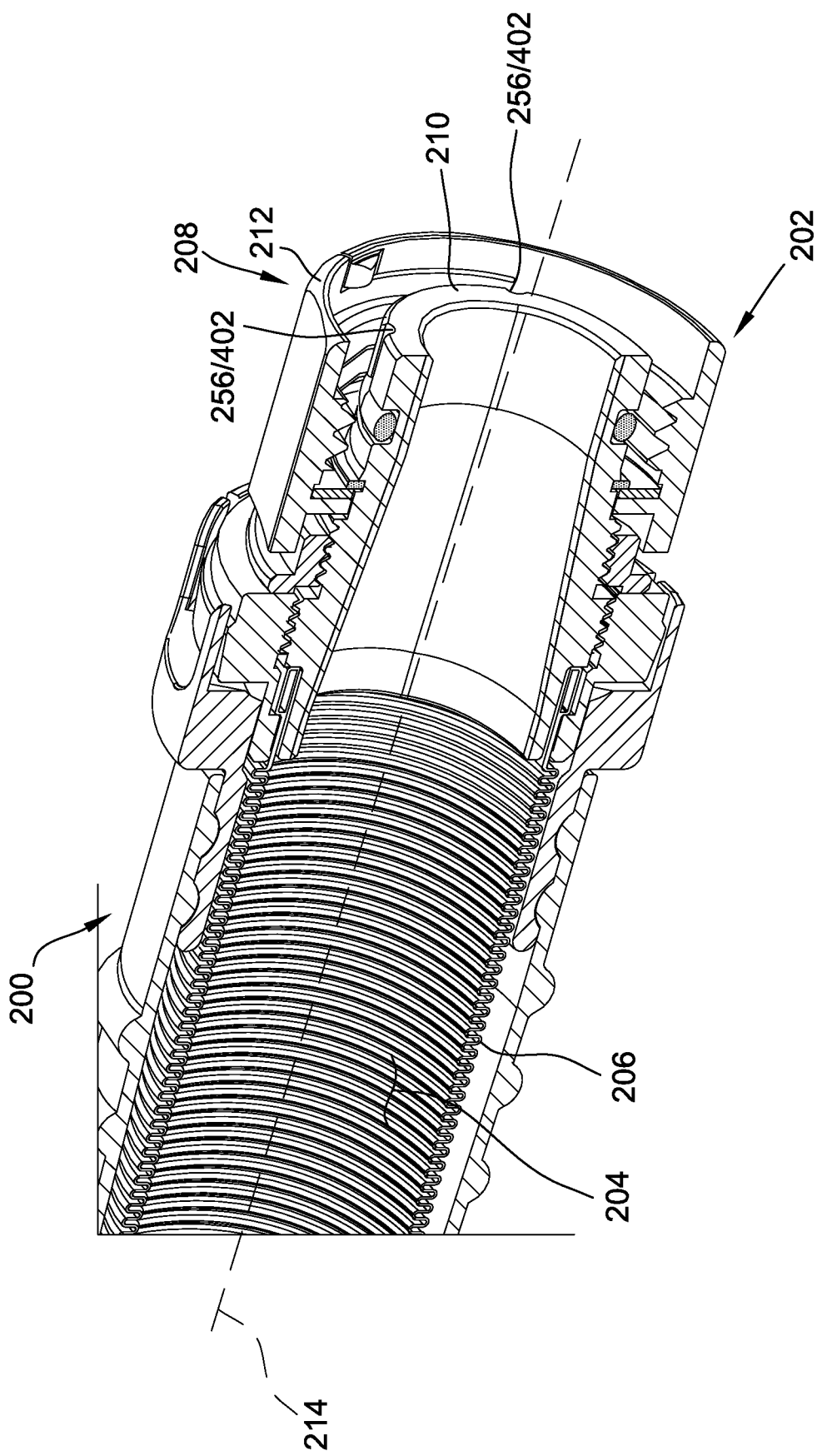
FIG. 6 is a perspective cut-away view the outflow cannula of FIG. 5.

FIG. 5 is a perspective view of an outflow cannula 200 and a portion of a pump housing 300 suitable for use in the blood pump assemblies 14 and 100 of FIGS. 1-4. FIG. 6 is a cut-away view of the outflow cannula 200, and FIG. 7 is a perspective view of the portion of the pump housing 300 shown in FIG. 5.

Figure 7:
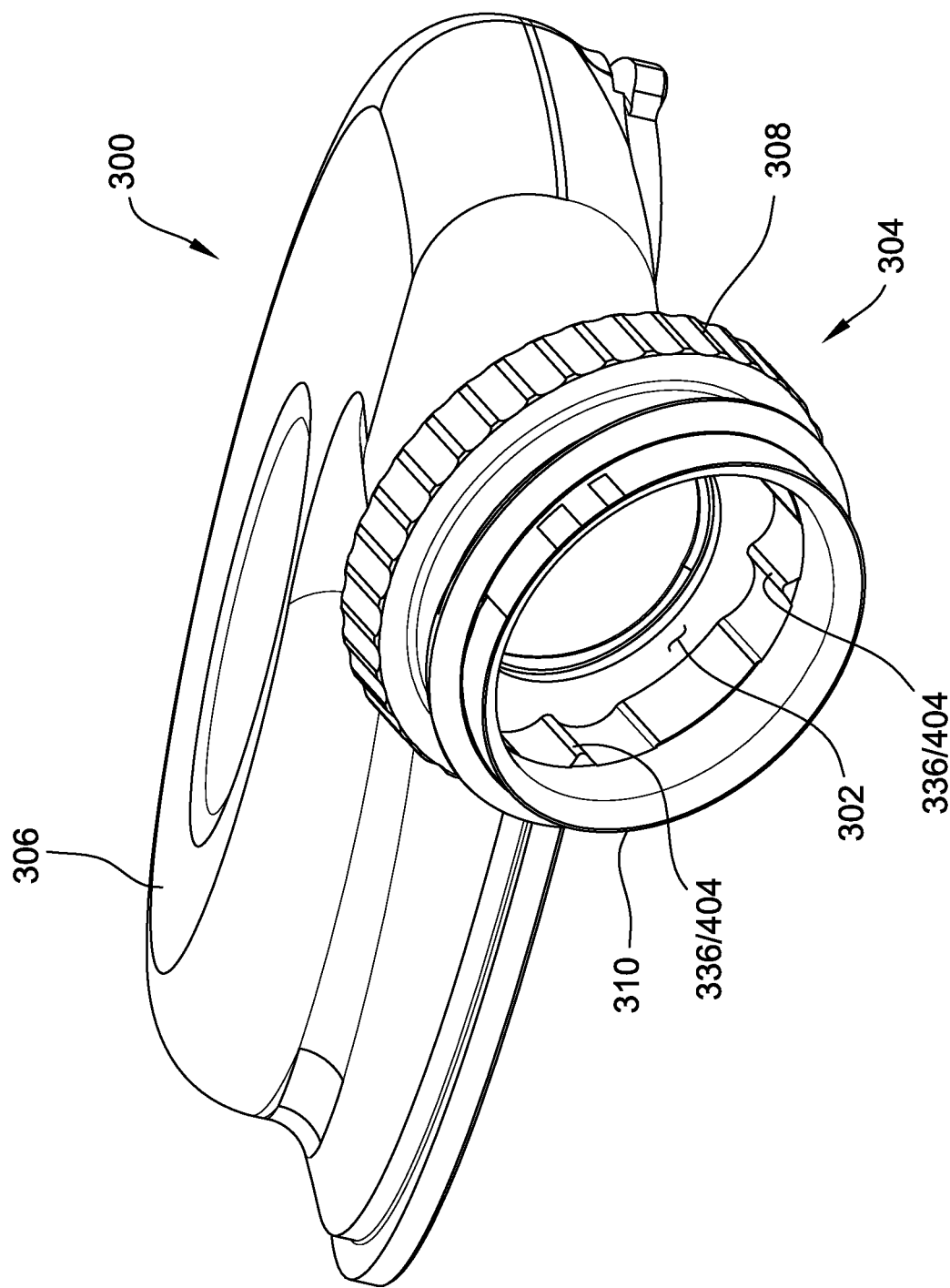
FIG. 7 is a perspective view of the portion of the pump housing shown in FIG. 5.

The portion of the pump housing 300 illustrated in FIGS. 5 and 7 defines an outlet 302 of the pump housing 300 (e.g., outlet 124), and includes an outlet coupler 304 located at the outlet 302. The outlet coupler 304 is selectively coupleable to the outflow cannula 200 and, as described further herein, cooperatively engages the outflow cannula 200 to form an anti-rotation mechanism 400 and an axial lock 500 (shown in FIG. 15) that inhibit or limit relative rotation and axial movement, respectively, of the outflow cannula 200 and the pump housing 300. The portion of the pump housing 300 illustrated in FIGS. 5 and 7 is a cap 306 of the pump housing 300, which may have substantially the same configuration and couple to the remainder of the pump housing 300 in substantially the same manner as cap 136 shown and described above with reference to FIG. 4. In other embodiments, the outlet coupler 304 and the outlet 302 of the pump housing 300 may be located on a portion of the pump housing 300 other than the cap 306.

The outflow cannula 200 has an inflow end 202 and an outflow end (not shown in FIGS. 5 and 6), and defines a fluid passage 204 extending therethrough. The inflow end 202 connects to the outlet 302 of the pump housing 300, and receives fluid pumped through the pump housing 300 and out of the outlet 302. The fluid travels through the fluid passage 204, and exits at the outflow end, which may be connected to the ascending or descending aorta.

Figure 8:
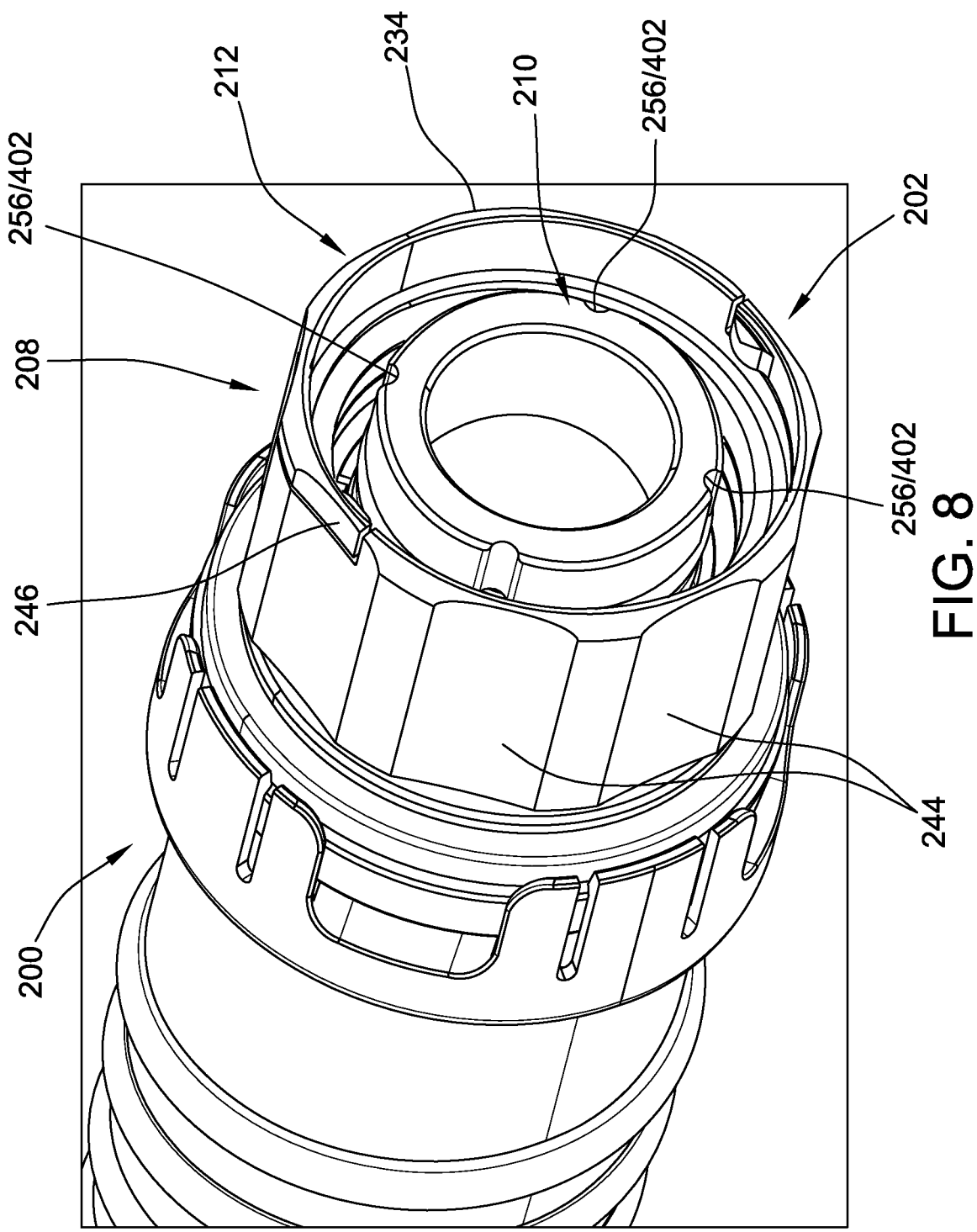
FIG. 8 is a perspective view of a coupler assembly of the outflow cannula of FIG. 5.

The outflow cannula 200 includes a flexible fluid conduit 206 that extends between the inflow end 202 and the outflow end, and at least partially defines the fluid passage 204. The fluid conduit 206 is constructed of suitably flexible materials such that the outflow cannula 200 can be manipulated by an operator (e.g., a surgeon) and conform to a patient's thoracic cavity. With additional reference to FIGS. 8 and 9, the outflow cannula 200 also includes a coupler assembly 208 that is coupled to the fluid conduit 206 at the inflow end 202 of the outflow cannula 200. The coupler assembly 208 is configured to be selectively and removably connected to the outlet coupler 304, for example, when the implantable blood pump assembly 100 is implanted in a patient.

In the illustrated embodiment, the coupler assembly 208 includes an adapter sleeve 210 and a screw ring 212 rotatably coupled to the adapter sleeve 210. The adapter sleeve 210 and screw ring 212 are co-axial with one another, and the screw ring 212 is configured to rotate about a longitudinal axis 214 of the outflow cannula 200 relative to the adapter sleeve 210 to facilitate coupling of the coupler assembly 208 to the outlet coupler 304.

The adapter sleeve 210 has a first end 216 sized to be received within the outlet 302 of the pump housing 300, and a second end 218 disposed within the fluid passage 204 defined by the fluid conduit 206. The adapter sleeve 210 has a suitably rigid construction, and is more rigid than the fluid conduit 206 to provide a secure mechanical connection to the pump housing 300. The adapter sleeve 210 may be constructed from any suitable material that enables the coupler assembly 208 to function as described herein, including, for example and without limitation, titanium, titanium alloys, stainless steel, and plastics of appropriate strength that are capable of sterilization and long term implantability. In the illustrated embodiment, the adapter sleeve 210 is coupled to the fluid conduit 206 by a threaded coupler 220, which is crimped on an end of the fluid conduit 206.

The adapter sleeve 210 also has an annular groove 222 defined in a radial outer surface 224 thereof at the first end 216 of the adapter sleeve 210. An annular seal 226 is disposed in the annular groove 222, and is configured to sealingly engage a portion of the outlet coupler 304 when the coupler assembly 208 is connected to the outlet coupler 304, as described further herein.

Figure 9:
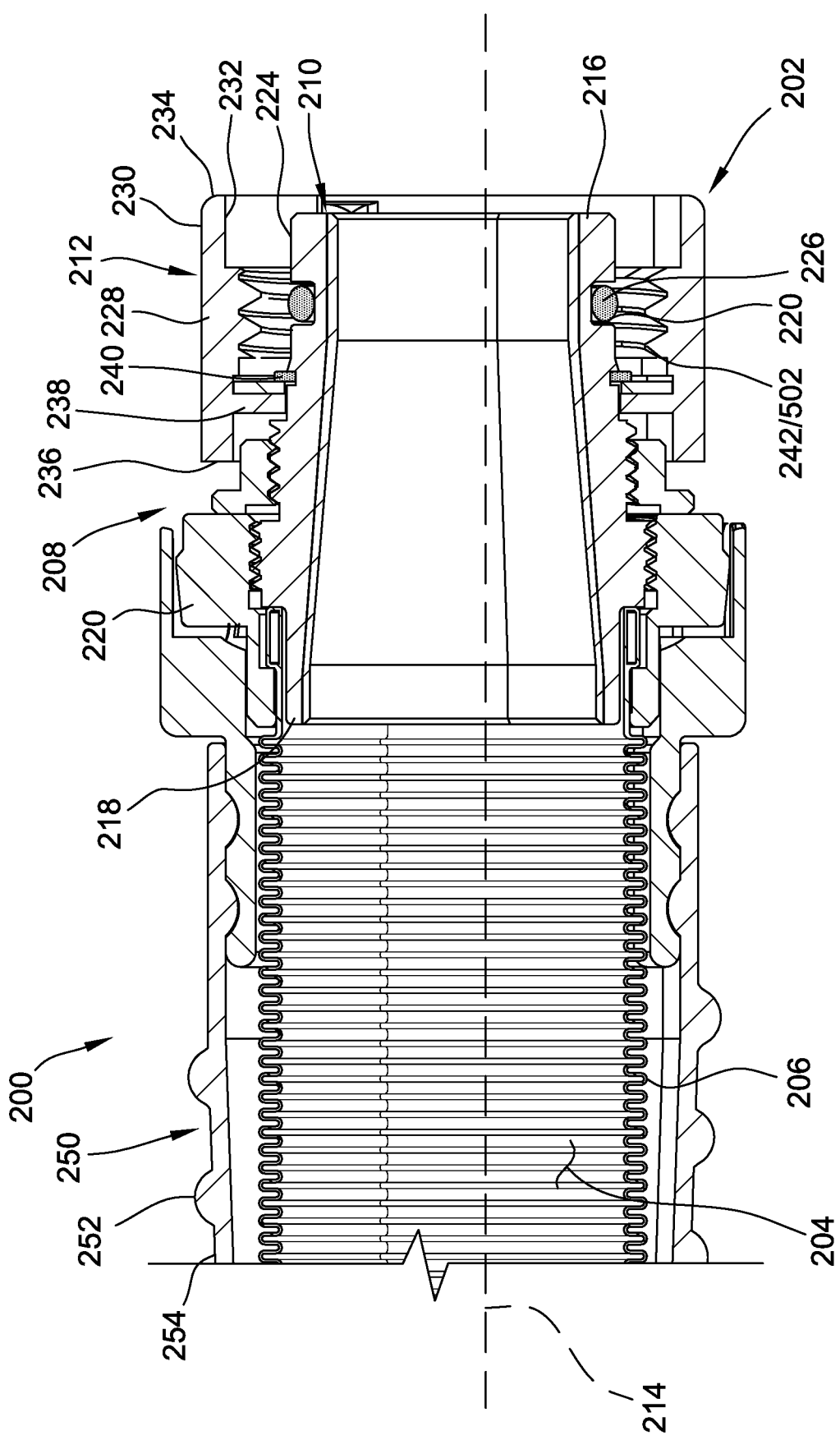
FIG. 9 is a cross-sectional view of the outflow cannula of FIG. 5.

The screw ring 212 includes a cylindrical sleeve 228 having a radial outer surface 230 and a radial inner surface 232. The screw ring 212 extends from a first, free end 234 to a second end 236 located downstream of (i.e., towards the outflow end of the outflow cannula 200) the first end 234. As shown in FIG. 9, the screw ring 212 extends axially past the first end 216 of the adapter sleeve 210.

The cylindrical sleeve 228 has an inner diameter greater than an outer diameter of the adapter sleeve 210, and extends around and encloses the first end 216 of the adapter sleeve 210. An annular flange 238 extends radially inwards from the radial inner surface 232 of the screw ring sleeve 228 to the radial outer surface 224 of the adapter sleeve 210 to rotatably couple the screw ring 212 to the adapter sleeve 210. A lock ring 240 is coupled to the radial outer surface 224 of the adapter sleeve 210 upstream of the annular flange 238 (i.e., towards the inflow end 202 of the outflow cannula 200), and inhibits axial movement of the screw ring 212 relative to the adapter sleeve 210.

The radial inner surface 232 of the screw ring sleeve 228 includes threads 242 along an axial portion thereof to facilitate connection of the outflow cannula 200 to the outlet coupler 304. The radial outer surface 230 of the screw ring sleeve 228 includes a plurality of finger grooves or indentations 244 (shown in FIG. 8) arranged circumferentially about the radial outer surface 230 to facilitate gripping or grasping the screw ring 212. In the illustrated embodiment, the screw ring 212 also includes a pair of detent tabs 246 (shown in FIG. 8) located at the first end 234 thereof. The detent tabs 246 are located diametrically opposite one another, and are configured to cooperatively engage the outlet coupler 304 to provide tactile feedback to an operator during connection of the outflow cannula 200 to the pump housing 300.

The screw ring 212 may be constructed from any suitable material that enables the coupler assembly 208 to function as described herein, including, for example and without limitation, titanium, titanium alloys, stainless steel, and plastics of appropriate strength that are capable of sterilization and long term implantability.

In the illustrated embodiment, the outflow cannula 200 also includes a reinforcing sleeve 250 (shown in FIGS. 5 and 9) coupled to the fluid conduit 206 at the inflow end 202 of the outflow cannula 200, and extending towards the outflow end. The reinforcing sleeve 250 has a stiffer construction than the fluid conduit 206, and is configured to inhibit excessive flexing of the fluid conduit 206 at the inflow end 202 and provide strain relief to the fluid conduit 206. The reinforcing sleeve 250 of the illustrated embodiment includes a helical spring 252 coupled to a sleeve 254, both of which enclose the fluid conduit 206. In other embodiments, the reinforcing sleeve 250 may have any suitable construction that enables the outflow cannula 200 to function as described herein. In yet other embodiments, the reinforcing sleeve 250 may be omitted from the outflow cannula 200.

Figure 10:
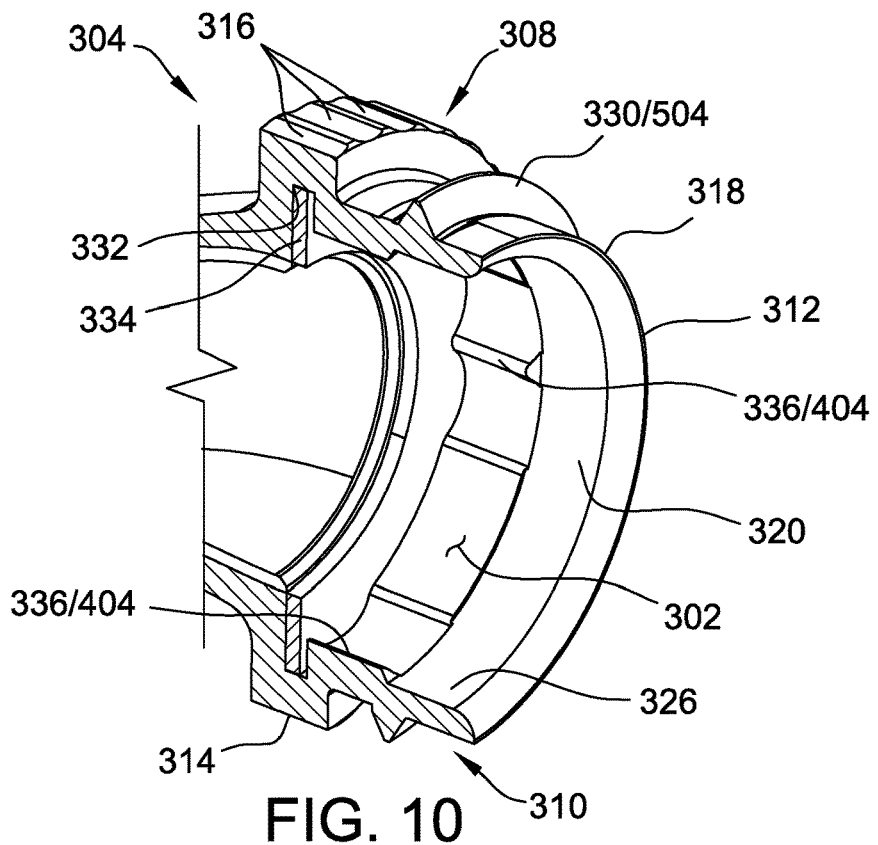
FIG. 10 is a cut-away view of an outlet coupler of the pump housing of FIG. 5.
Figure 11:
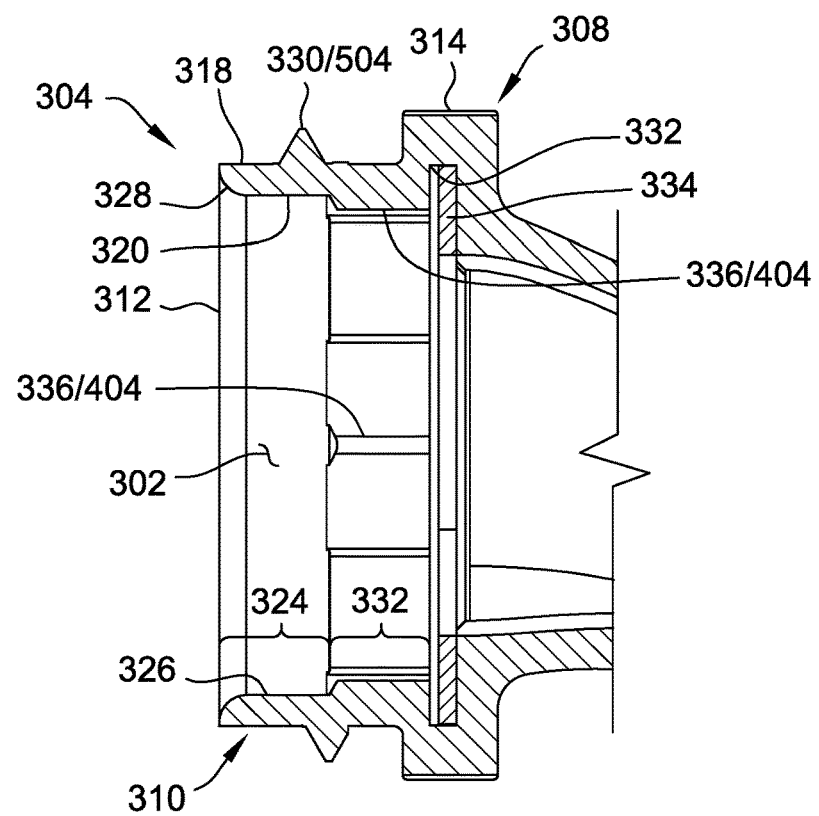
FIG. 11 is a cross-sectional view of the outlet coupler of FIG. 10.

With additional reference to FIGS. 10 and 11, the outlet coupler 304 includes a collar 308 and a sleeve 310 extending axially outward and downstream from (i.e., away from the pump housing 300) the collar 308 to a free end 312. The collar 308 extends radially outwards from the pump housing 300 (specifically, from the cap 306), and includes a radial outer surface 314 defining a plurality of indentations or grooves 316. The outlet coupler sleeve 310 includes a radial outer surface 318 and a radial inner surface 320 that defines the outlet 302 of the pump housing 300.

The radial inner surface 320 of the outlet coupler sleeve 310 includes a first axial portion 322 and a second axial portion 324 (labeled in FIG. 11). The first axial portion 322 extends from the collar 308, and is located upstream of (i.e., closer to the flow path defined by the pump housing 300) the second axial portion 324. The second axial portion 324 extends from the first axial portion 322 to the free end 312 of the sleeve 310, and defines a sealing surface 326 that sealingly engages the annular seal 226 during insertion of the outflow cannula 200 into the housing outlet 302. As shown in FIG. 11, the second axial portion 324 includes a chamfered edge 328 at the free end 312 of the sleeve 310, which facilitates insertion of and engagement with the annular seal 226.

In the illustrated embodiment, the radial outer surface 318 of the sleeve 310 includes threads 330 that cooperatively engage the threads 242 of the screw ring 212 to secure the coupler assembly 208 to the outlet coupler 304. Also, in the illustrated embodiment, an annular groove 332 is defined by the collar 308 and extends radially outwards from the first axial portion 322 of the radial inner surface 320. A washer 334 is disposed in the annular groove 332, and sealingly engages the first end 216 of the adapter sleeve 210 when the outflow cannula 200 is inserted into the outlet 302.

The outlet coupler 304 may be constructed of any suitable material that enables the outlet coupler to function as described herein. In some embodiments, the outlet coupler 304 is constructed from the same or similar materials as the pump housing 300 (e.g., the cap 306). Suitable materials from which the outlet coupler 304 may be constructed include, for example and without limitation, titanium, titanium alloys, stainless steel, and plastics of appropriate strength that are capable of sterilization and long term implantability.

Figure 12:
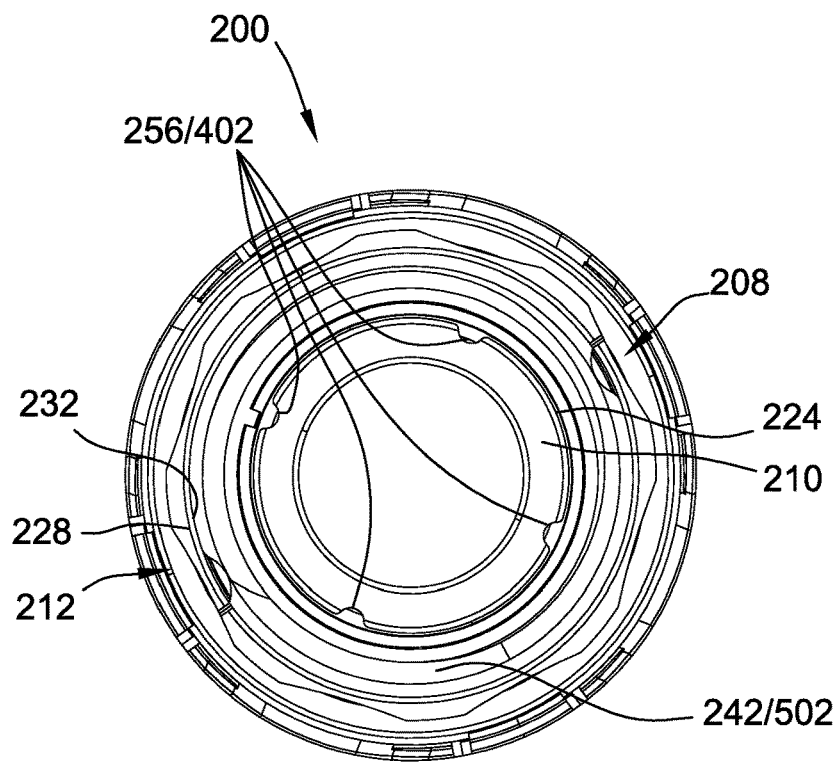
FIG. 12 is an end view of the outflow cannula of FIG. 5.
Figure 13:
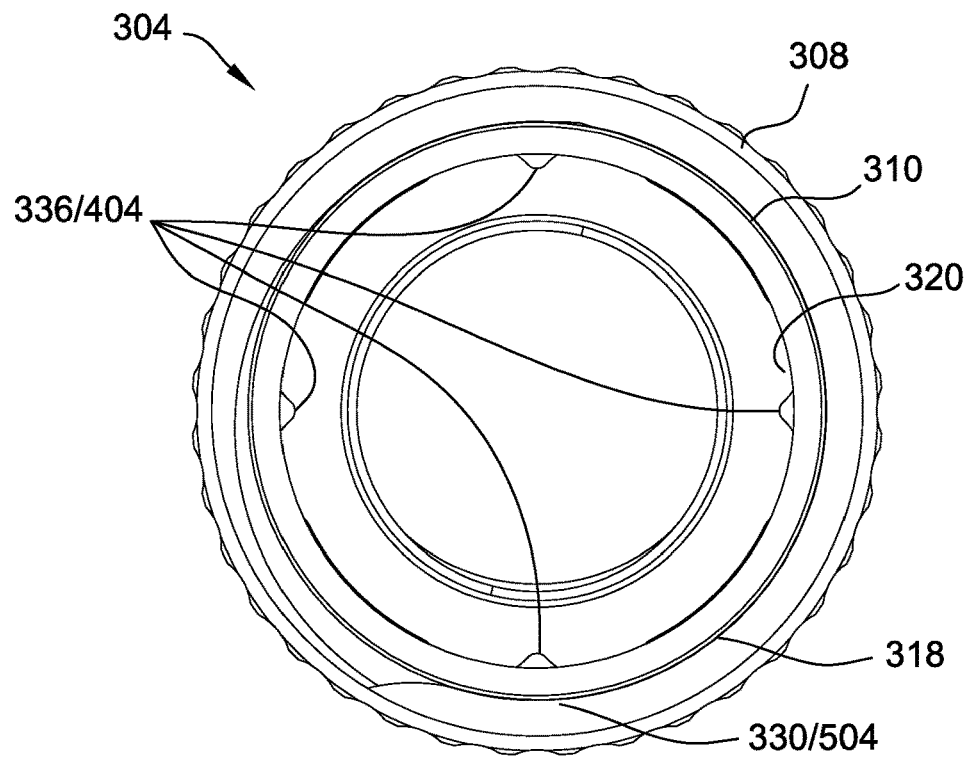
FIG. 13 is an end view of the outlet coupler of FIG. 10.
Figure 14:
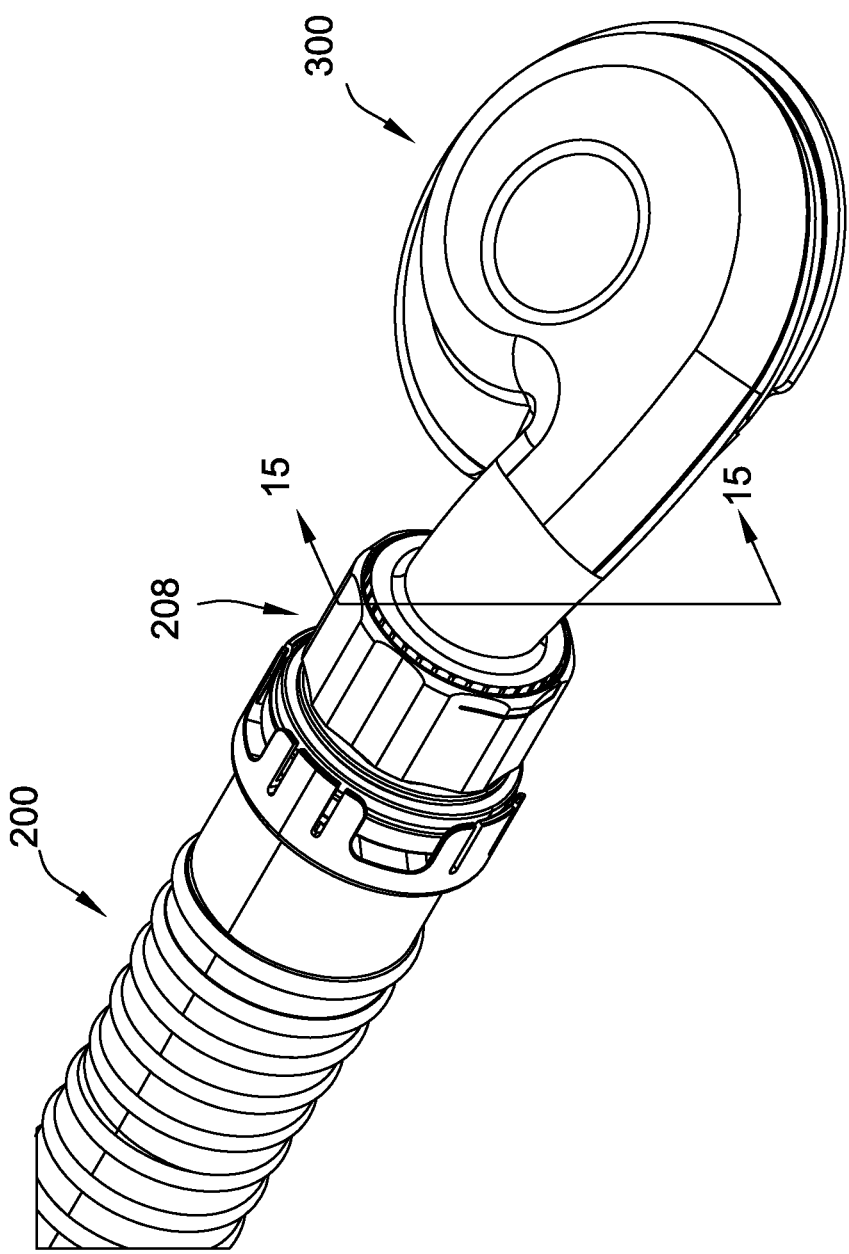
FIG. 14 is perspective view of the outflow cannula connected to the portion of the pump housing shown in FIG. 5.
Figure 15:
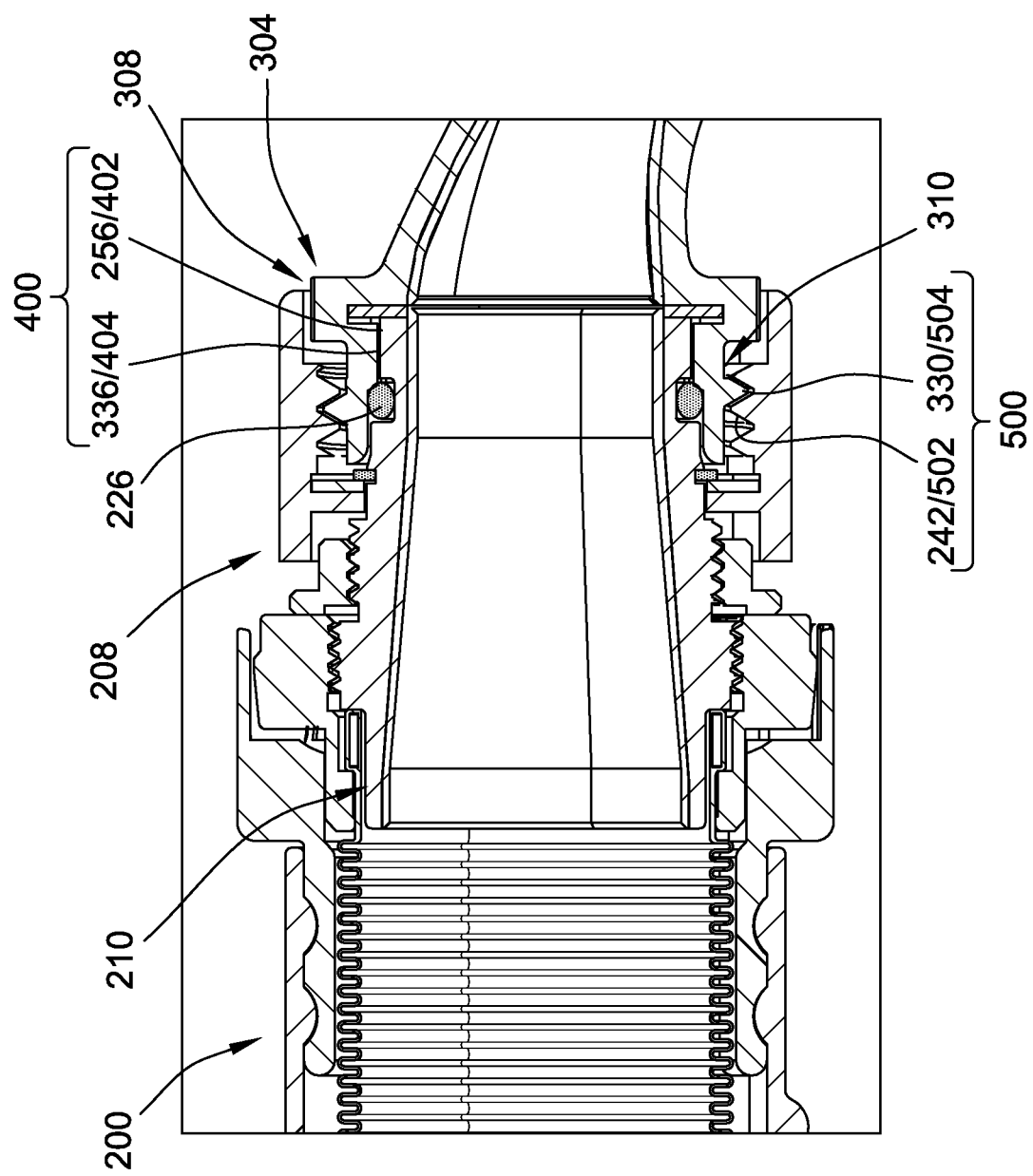
FIG. 15 is a cross-sectional view of the outflow cannula and the pump housing of FIG. 14, taken along line "15-15" in FIG. 14.

FIG. 12 is an end view of the outflow cannula 200, and FIG. 13 is an end view of the outlet coupler 304. FIG. 14 is a perspective view of the outflow cannula 200 connected to the pump housing 300, and FIG. 15 is a cross-sectional view taken along line "15-15" in FIG. 14. With additional reference to FIGS. 12-15, the coupler assembly 208 includes a first component 402 of the anti-rotation mechanism 400 and a first component 502 of the axial lock 500, and the outlet coupler 304 includes a second component 404 of the anti-rotation mechanism 400 and a second component 504 of the axial lock 500. The first and second components 402, 404 of the anti-rotation mechanism 400 are configured for mating engagement with one another, and inhibit or limit rotation of the outflow cannula 200 relative to the pump housing 300 when engaged. The first and second components 502, 504 of the axial lock 500 are configured for mating engagement with one another, and inhibit axial movement of the outflow cannula 200 relative to the pump housing 300 when engaged.

Additionally, as shown in FIG. 15, the first and second components 402, 404 of the anti-rotation mechanism 400 are positioned relative to the first and second components 502, 504 of the axial lock 500 such that the first and second components 402, 404 of the anti-rotation mechanism 400 engage one another prior to the first and second components 502, 504 of the axial lock 500, during insertion of the outflow cannula 200 into the housing outlet 302. In other words, during assembly, the outflow cannula 200 is rotationally locked relative to the pump housing 300 prior to the outflow cannula 200 being axially fixed or locked to the pump housing 300 as a result of the configuration of the anti-rotation mechanism 400 and the axial lock 500. As a result, the outflow cannula 200 is rotationally locked or fixed during implantation of the blood pump assembly 100, prior to the outflow cannula 200 being axially locked or secured to the pump housing 300, and is therefore inhibited from post-operative rotation. The anti-rotation mechanism 400 and axial lock 500 thereby facilitate preventing excessive post-operative rotation and torsion of the outflow cannula 200, and the risk of narrowing or collapsing of the fluid conduit 206 of the outflow cannula 200 resulting from such post-operative rotation and torsion.

Figure 16:
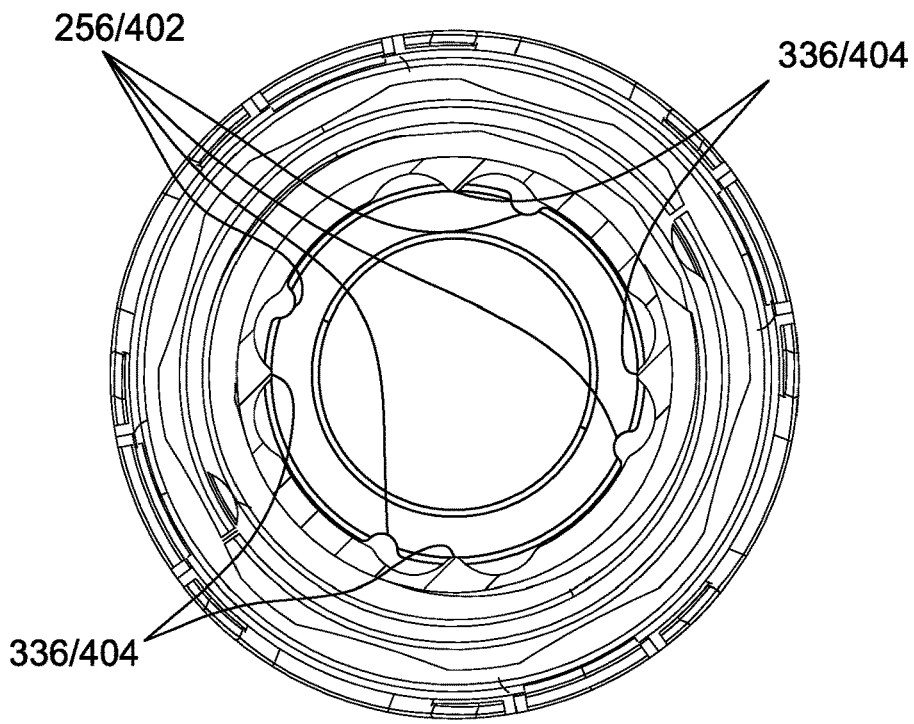
FIG. 16 is a cross-sectional view of the outflow cannula and the pump housing of FIG. 5, taken along line "16-16" in FIG. 5.
Figure 17:
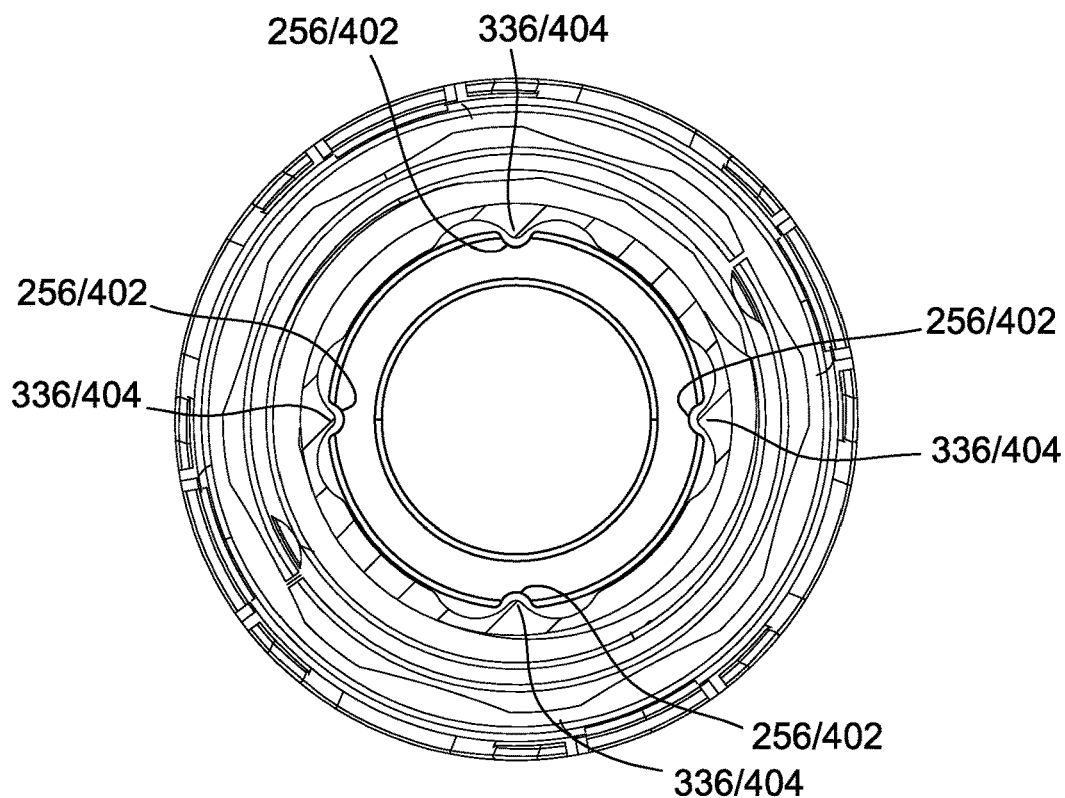
FIG. 17 is another cross-sectional view of the outflow cannula and the pump housing shown in FIG. 16, illustrating the outflow cannula and the pump housing in an aligned state.

Further, in the illustrated embodiment, the first and second components 402, 404 of the anti-rotation mechanism 400 inhibit engagement of the first and second components 502, 504 of the axial lock 500 when the first and second components 402, 404 of the anti-rotation mechanism 400 are axially out of alignment. For example, if the first and second components 402, 404 of the anti-rotation mechanism 400 are axially out of alignment, as shown in FIG. 16, they will prevent insertion of the outflow cannula 200 into the housing outlet 302 such that the first and second components 502, 504 of the axial lock 500 cannot engage one another. The first and second components 402, 404 of the anti-rotation mechanism 400 will permit insertion of the outflow cannula 200 into the housing outlet 302 only when the first and second components 402, 404 of the anti-rotation mechanism 400 are axially aligned with one another, as shown in FIG. 17. In this way, the anti-rotation mechanism 400 ensures that the first and second components 402, 404 of the anti-rotation mechanism 400 are engaged prior to the first and second components 502, 504 of the axial lock 500, thereby reducing the risk of the mating components seizing without the anti-rotation mechanism 400 being engaged.

Additionally, the first and second components 402, 404 of the anti-rotation mechanism 400 are arranged relative to one another such that the outflow cannula 200 is selectively coupleable to the outlet coupler 304 in one of a discrete, limited number of orientations. In some embodiments, for example, the anti-rotation mechanism 400 permits connection of the coupler assembly 208 to the outlet coupler 304 in at least 2 orientations, at least 4 orientations, at least 10 orientations, between 1 and 100 orientations, between 1 and 50 orientations, between 1 and 40 orientations, between 1 and 30 orientations, between 1 and 20 orientations, between 1 and 10 orientations, between 1 and 5 orientations, between 2 and 20 orientations, between 2 and 10 orientations, and between 2 and 5 orientations. In the illustrated embodiment, the anti-rotation mechanism 400 permits the coupler assembly 208 to be connected to the outlet coupler 304 in one of 4 discrete orientations. In other embodiments, the anti-rotation mechanism 400 may permit coupling of the coupler assembly 208 and the outlet coupler 304 in any other number of orientations. By limiting the number of orientations in which the coupler assembly 208 can be connected to the outlet coupler 304, the anti-rotation mechanism 400 further facilitates preventing excessive rotation and torsion of the outflow cannula 200, particularly during implantation of the blood pump assembly 100, by limiting the extent to which the outflow cannula 200 can be rotated relative to the pump housing 300 and still be connected.

In the illustrated embodiment, the first end 216 of the adapter sleeve 210 includes the first component 402 of the anti-rotation mechanism 400, and the outlet coupler 304 includes the second component 404 of the anti-rotation mechanism 400. More specifically, in the illustrated embodiment, the first component 402 of the anti-rotation mechanism 400 includes a plurality of longitudinally-extending grooves 256, and the second component of the anti-rotation mechanism 400 includes a plurality of longitudinally-extending splines 336.

The grooves 256 are defined in the radial outer surface 224 of the adapter sleeve 210 at the first end 216 thereof. The grooves 256 extend downstream from the first end 216 (i.e., towards the second end 218 of the adapter sleeve 210) to the annular groove 222 in which the annular seal 226 is positioned. The plurality of grooves 256 are spaced circumferentially about the radial outer surface 224 of the adapter sleeve 210 at distances that correspond to the circumferential spacing of the plurality of splines 336. The illustrated embodiment includes 4 grooves 256 spaced at 90° intervals relative to adjacent grooves 256. In other embodiments, the coupler assembly 208 may include more than or less than 4 grooves, including, for example and without limitation, at least 1 groove, at least 2 grooves, at least 4 grooves, at least 10 grooves, between 1 groove and 100 grooves, between 1 groove and 50 grooves, between 1 groove and 40 grooves, between 1 groove and 30 grooves, between 1 groove and 20 grooves, between 1 groove and 10 grooves, between 1 groove and 5 grooves, between 2 grooves and 20 grooves, between 2 grooves and 10 grooves, and between 2 grooves and 5 grooves. Further, although the grooves 256 are shown and described as being equally spaced about the radial outer surface 224 of the adapter sleeve 210, the grooves 256 may be spaced at unequal intervals in other embodiments. For example, 4 grooves may be arranged such that each groove 256 is spaced 60° from one adjacent groove 256, and 120° from the other adjacent groove 256. This can have the effect of further limiting the number of orientations in which the coupler assembly 208 may be connected to the outlet coupler 304.

Additionally, in the illustrated embodiment, the grooves 256 are spanner nut grooves configured for engagement with a spanner wrench. In particular, each groove 256 is sized and shaped to receive a leg or spline of a spanner wrench to apply torque to the adapter sleeve 210 during assembly of the outflow cannula 200. In this way, the grooves 256 provide multiple functions in assembly of the blood pump assembly 100, and reduce the need for additional components to serve these functions, thereby reducing the size, number, and cost of components of the outflow cannula 200. In other embodiments, the grooves 256 may be configured as grooves other than spanner nut grooves.

The plurality of splines 336 are located on the radial inner surface 320 of the outlet coupler sleeve 310, specifically along the first axial portion 322 of the radial inner surface 320, and are configured for mating engagement with the plurality of grooves 256. As shown in FIG. 13, each spline 336 protrudes radially inward from the radial inner surface 320, and extends further radially inward than the second axial portion 324 of the radial inner surface 320.

Similar to the grooves 256, the plurality of splines 336 are spaced circumferentially about the radial inner surface 320 of the sleeve 310 at distances that correspond to the circumferential spacing of the plurality of grooves 256. The illustrated embodiment includes 4 splines 336 spaced at 90° intervals relative to adjacent splines 336. In other embodiments, the outlet coupler 304 may include more than or less than 4 splines, including, for example and without limitation, at least 1 spline, at least 2 splines, at least 4 splines, at least 10 splines, between 1 spline and 100 splines, between 1 spline and 50 splines, between 1 spline and 40 splines, between 1 spline and 30 splines, between 1 spline and 20 splines, between 1 spline and 10 splines, between 1 spline and 5 splines, between 2 splines and 20 splines, between 2 splines and 10 splines, and between 2 splines and 5 splines. Further, although the splines 336 are shown and described as being equally spaced about the radial inner surface 320 of the outlet coupler sleeve 310, the splines 336 may be spaced at unequal intervals in other embodiments. For example, 4 splines may be arranged such that each spline 336 is spaced 60° from one adjacent spline 336, and 120° from the other adjacent spline 336. This can have the effect of further limiting the number of orientations in which the coupler assembly 208 may be connected to the outlet coupler 304.

Each spline 336 is sized and shaped complementary to one of the grooves 256. In the illustrated embodiment, each spline 336 has an arcuate or rounded cross-section, and each groove 256 has a complementary arcuate or rounded cross-section. The arcuate shape of the splines 336 and grooves 256 facilitates reducing shear forces between components (e.g., the adapter sleeve 210 and the outlet coupler 304) resulting from rotational forces imparted on the components during assembly of the blood pump assembly 100 and/or after assembly (i.e., post-operatively). Additionally, because the splines 336 and grooves 256 are spaced and arranged circumferentially, rotational forces imparted on components of the blood pump assembly 100 have the effect of re-centering or re-aligning the adapter sleeve 210 and the outlet coupler 304.

The plurality of splines 336 can be constructed integrally with the outlet coupler 304. That is, the splines 336 may be fabricated and formed integrally with the outlet coupler 304 during fabrication of the outlet coupler 304 (e.g., by molding, machining, milling, etc.). Alternatively, the plurality of splines 336 may be formed on an insert (e.g., a ring-shaped insert) sized and shaped to be received within the outlet coupler sleeve 310.

In the illustrated embodiment, the first and second components 402, 404 of the anti-rotation mechanism 400 are configured to substantially inhibit any rotation of the outflow cannula 200 relative to the pump housing 300 about longitudinal axis 214. For example, each groove 256 has an arc length or circumferential width that is substantially equal to, but slightly larger than, the arc length or circumferential width of each spline 336 such that the grooves 256 provide just enough clearance for the splines 336 to be inserted into the grooves 256. Once the splines 336 are inserted into the grooves 256, rotation of the outflow cannula 200 relative to the pump housing 300 is substantially inhibited due to lateral engagement of the splines 336 with the grooves 256. For example, the splines 336 and grooves 256 in the illustrated embodiment may limit relative rotation of the outflow cannula 200 and the pump housing 300 to less than 2°, less than 1°, or even less than 0.5°. In other embodiments, the first and second components 402, 404 of the anti-rotation mechanism 400 can be configured to permit limited rotation of the outflow cannula 200 relative to the pump housing 300. In some embodiments, for example, the first and second components 402, 404 of the anti-rotation mechanism 400 can be configured to permit rotation of the outflow cannula 200 (specifically, the adapter sleeve 210 and fluid conduit 206) relative to the pump housing 300 by up to 10° (±5° from center), up to 20° (±10° from center), up to 30° (±15° from center), up to 40° (±20° from center), up to 50° (±25° from center), up to 60° (±30° from center), and even up to 90° (±45° from center). By way of example, the arc length or circumferential width of the grooves 256 can be sized larger than the arc length or circumferential width of the splines 336 by a suitable amount to achieve a desired amount of controlled rotation of the outflow cannula 200 relative to the pump housing 300. In such embodiments, the screw ring 212 would remain axially and rotationally fixed relative to the outlet coupler 304, while the adapter sleeve 210 and fluid conduit 206 would be permitted to rotate by a limited amount. Allowing limited rotation of the outflow cannula 200 relative to the pump housing 300 can provide additional, post-operative strain relief for the outflow cannula 200, for example, to accommodate movement of the patient.

In this embodiment, the first and second components 502, 504 of the axial lock include complementary threads. Specifically, the first component 502 of the axial lock 500 includes the threads 242 on the radial inner surface 232 of the screw ring sleeve 228, and the second component 504 of the axial lock 500 includes the threads 330 on the radial outer surface 318 of the outlet coupler sleeve 310.

Figure 18:
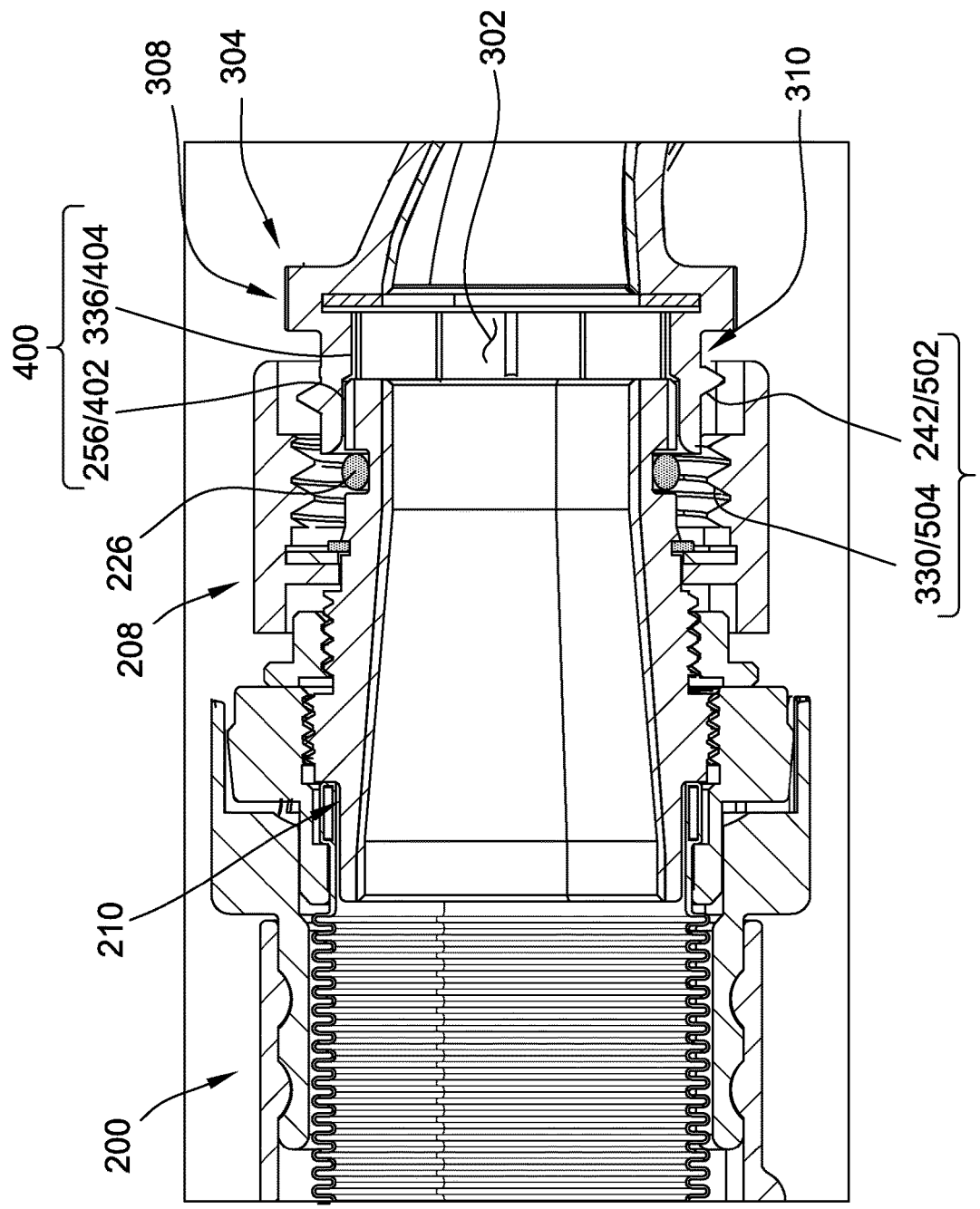
FIG. 18 is another cross-sectional view of the outflow cannula and the pump housing shown in FIG. 15 during a first step of assembly.
Figure 19:
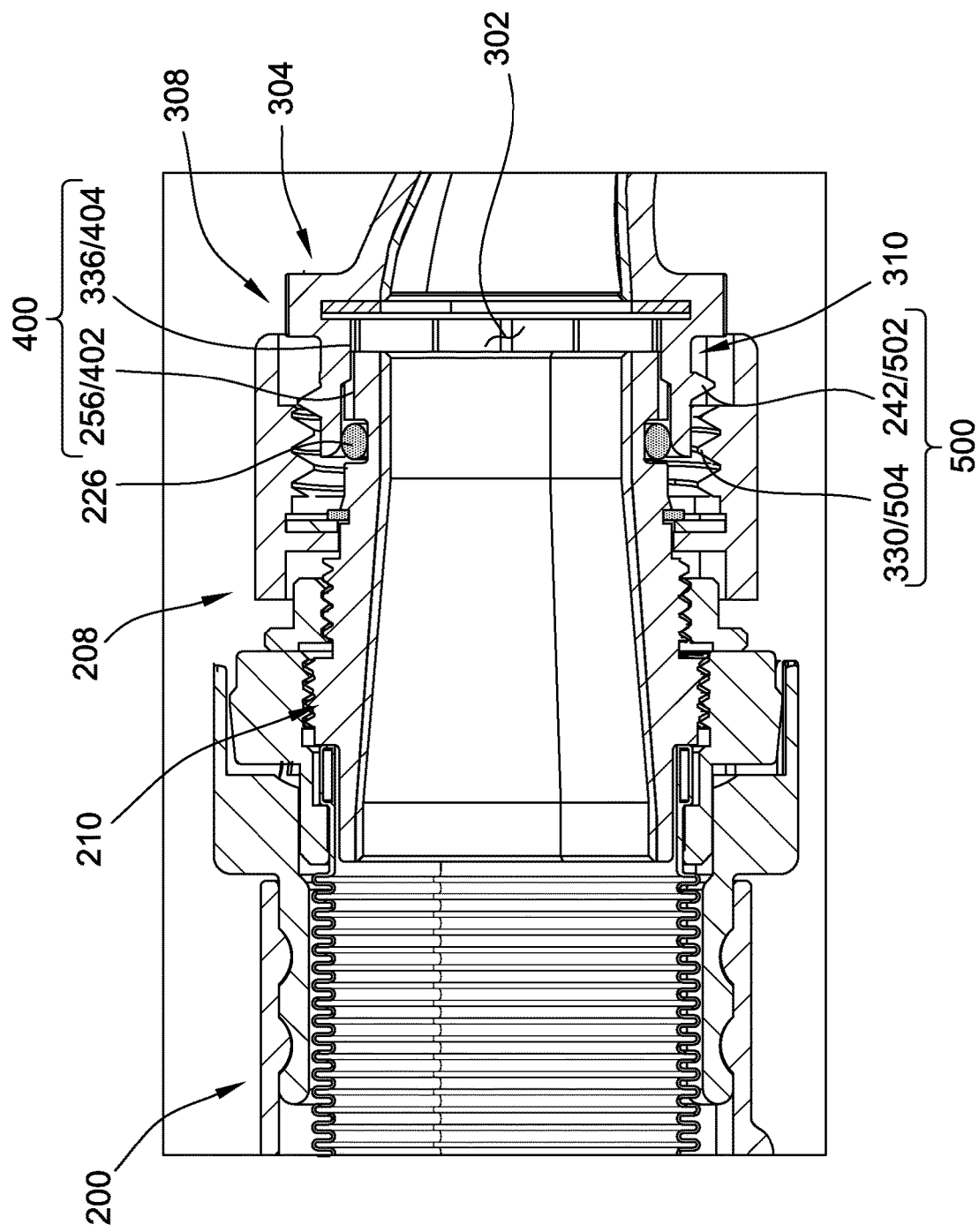
FIG. 19 is another cross-sectional view of the outflow cannula and the pump housing shown in FIG. 18 during a second step of assembly.

As noted above, the components of the anti-rotation mechanism 400 and the axial lock 500 are configured such that the components of the anti-rotation mechanism 400 engage one another prior to the components of the axial lock 500 engaging one another during insertion of the outflow cannula 200 into the housing outlet 302. In the illustrated embodiment, this is achieved based on the positioning of the grooves 256, splines 336, and threads 242, 330. Namely, the axial spacing of the splines 336 relative to the threads 330 on the radial outer surface 318 of the outlet coupler sleeve 310, and the grooves 256 relative to the threads 242 on the radial inner surface 232 of the screw ring sleeve 228, enable the splines 336 and grooves 256 to engage one another and form the anti-rotation mechanism 400 prior to the threads 242, 330 engaging one another. As illustrated in FIGS. 18 and 19, for example, as the outflow cannula 200 is inserted into the housing outlet 302, the splines 336 of the outlet coupler 304 will initially engage the grooves 256 of the adapter sleeve 210, prior to the threads 242, 330 engaging one another. Further, if the splines 336 and grooves 256 are not axially aligned (as shown in FIG. 16, for example), the splines 336 will engage the first end 216 of the adapter sleeve 210, and inhibit further insertion of the outflow cannula 200 into the housing outlet 302. This engagement between the first end 216 of the adapter sleeve 210 and the splines 336 of the outlet coupler 304 can provide useful tactile feedback to an operator, for example, by indicating that the adapter sleeve 210 is partially inserted into the outlet coupler 304, and the splines 336 and grooves 256 are not axially aligned.

When the splines 336 are axially aligned with the grooves 256 (as shown in FIG. 17, for example), the outflow cannula 200 can be further inserted into the housing outlet 302 such that the splines 336 are received within and engage the grooves 256. As shown in FIG. 19, the splines 336 engage the grooves 256 prior to the threads 242, 330 engaging one another. Continued insertion of the outflow cannula 200 into the housing outlet 302 allows the threads 242, 330 to engage one another. When the threads 242, 330 initially engage one another, the threads 242, 330 will inhibit continued axially movement of the outflow cannula 200 relative to the pump housing 300. This initial engagement of the threads 242, 330 provides useful tactile feedback to an operator, for example, by providing an indication of the relative axial position of the outflow cannula 200 and the pump housing 300 and indicating that the threads 242, 330 are engaged such that the screw ring 212 can be rotated. Rotation of the screw ring 212 allows the threads 242, 330 to engage one another and provide a mechanical advantage in further inserting the outflow cannula 200 into the housing outlet 302, and engaging the annular seal 226 with the sealing surface 326. In the illustrated embodiment, continued rotation of the screw ring 212 results in engagement of the detent tabs 246 on the screw ring 212 with the grooves 316 in the collar 308 of the outlet coupler 304. Engagement of the detent tabs 246 with the grooves of the collar 308 provides tactile feedback to an operator to indicate that the outflow cannula 200 has been inserted to a sufficient depth into the housing outlet 302.

In the illustrated embodiment, the annular seal 226 is positioned relative to the grooves 256 and splines 336 such that the annular seal 226 engages the sealing surface 326 subsequent to the splines 336 engaging the grooves 256 (i.e., subsequent to the first and second components 402, 404 of the anti-rotation mechanism 400 engaging one another). Further, in the illustrated embodiment, the annular seal 226 is positioned relative to the threads 242, 330 and the sealing surface 326 such that the annular seal 226 engages the sealing surface 326 prior to the threads 242, 330 engaging one another (i.e., prior to the first and second components 502, 504 of the axial lock 500 engaging one another). In other embodiments, the annular seal 226 may be positioned relative to the threads 242, 330 and the sealing surface 326 such that the annular seal 226 engages the sealing surface 326 only after the threads 242, 330 engage one another (i.e., subsequent to the first and second components 502, 504 of the axial lock 500 engaging one another).

Although the components of anti-rotation mechanism 400 are shown and described as splines and grooves, it should be understood that the components of the anti-rotation mechanism 400 are not limited to the splines and grooves described herein. In particular, the components of the anti-rotation mechanism 400 may include any suitable components that enable the anti-rotation mechanism 400 to function as described herein, including, for example and without limitation, tabs, slots, protrusions, keyed components, bayonet-type connections, detents, serrations, knurling, reeding, teeth (e.g., a Hirth joint), clutch mechanisms, and combinations thereof. As used herein, the term "clutch mechanisms" includes, for example and without limitation, elements that generate radial compressive forces on one or both of the adapter sleeve 210 and the outlet coupler 304 as a result of a tensile load on one or both of the adapter sleeve 210 and the outlet coupler 304, (e.g. push-to-connect fittings), and elements that generate radial and/or axial compression forces on one or both of the adapter sleeve 210 and the outlet coupler 304 as a result of engagement of the axial lock 500 (e.g. a bolted connection with adequate friction at the mating interfaces).

Similarly, while the components of the axial lock 500 are shown and described as complementary threads, it should be understood that the components of the axial lock 500 are not limited to the threads described herein. In particular, the components of the axial lock 500 may include any suitable components that enable the axial lock 500 to function as described herein, including, for example and without limitation, snap-fit components, press-fit components, bayonet-type connections, detents, cam and groove connections, claw and flange connections, push-to-connect fittings, and combinations thereof.

Moreover, although the first component 402 of the anti-rotation mechanism 400 is shown and described as being part of the adapter sleeve 210, and the second component 404 of the anti-rotation mechanism 400 is shown and described as being part of the outlet coupler 304, it should be understood that the first and second components 402, 404 of the anti-rotation mechanism 400 may be reversed in other embodiments. That is, the adapter sleeve 210 may include the second component 404 of the anti-rotation mechanism 400, and the outlet coupler 304 may include the first component 402 of the anti-rotation mechanism 400. In yet other embodiments, the first and second components 402, 404 of the anti-rotation mechanism 400 may be located on components of the outflow cannula 200 and pump housing 300 other than the adapter sleeve 210 and the outlet coupler 304. Similarly, the first and second components 502, 504 of the axial lock 500 may be reversed in other embodiments. That is, the screw ring 212 may include the second component 504 of the axial lock 500, and the outlet coupler 304 may include the first component 502 of the axial lock. In yet other embodiments, the first and second components 502, 504 of the axial lock 500 may be located on components of the outflow cannula 200 and pump housing 300 other than the screw ring 212 and the outlet coupler 304.

Figure 20:
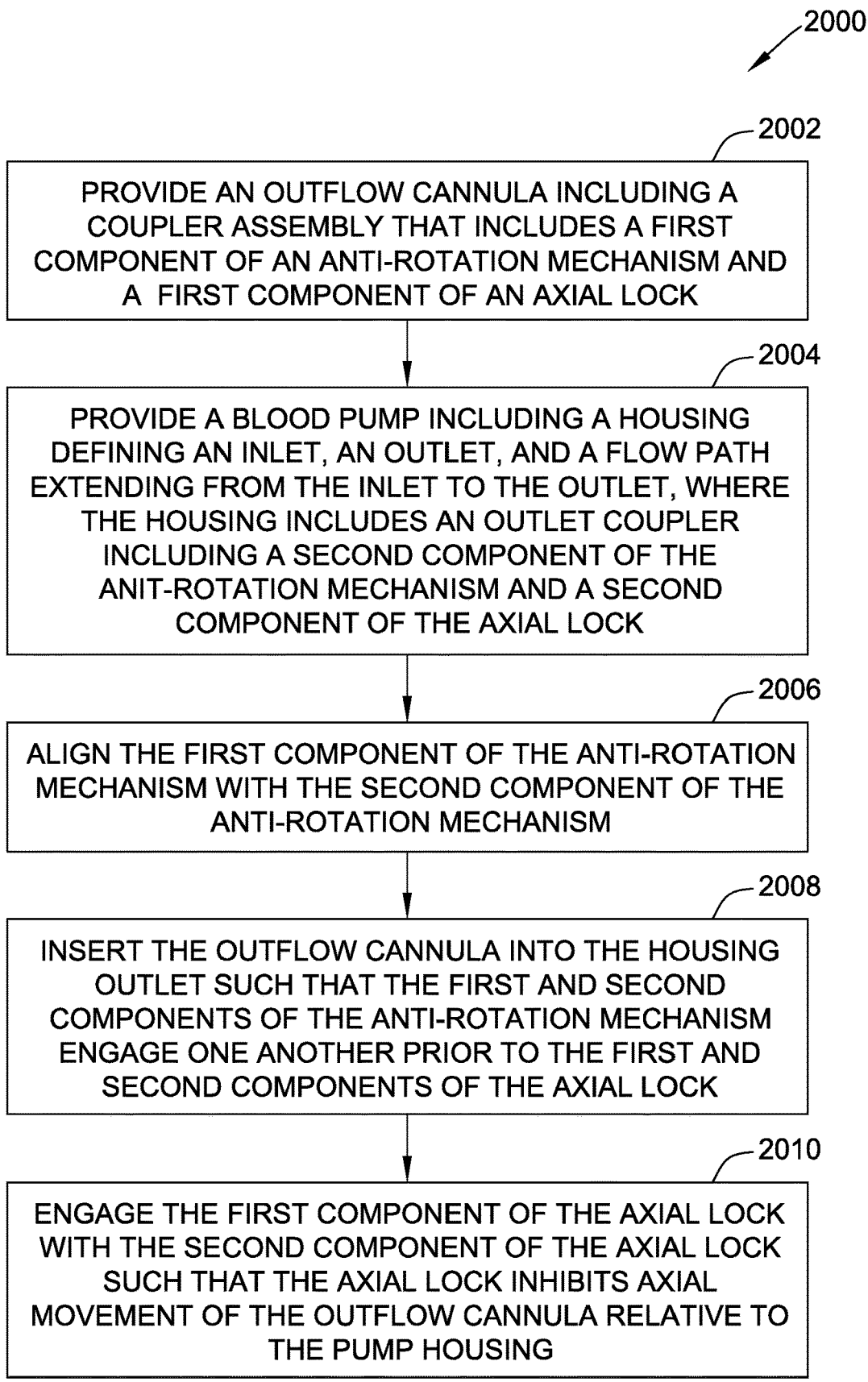
FIG. 20 is a flow diagram illustrating one embodiment of a method of assembling a blood pump assembly.

FIG. 20 is a flow diagram illustrating one embodiment of a method 2000 of assembling an implantable blood pump (e.g., the blood pump assembly 100). In the illustrated embodiment, the method 2000 includes providing 2002 an outflow cannula (e.g., outflow cannula 200) including a coupler assembly (e.g., coupler assembly 208) that includes a first component of an anti-rotation mechanism (e.g., first component 402 of anti-rotation mechanism 400) and a first component of an axial lock (e.g., first component 502 of axial lock 500). The method 2000 also includes providing 2004 a blood pump (e.g., blood pump 102) including a housing (e.g., blood pump housing 300) defining an inlet, an outlet, and a flow path extending from the inlet to the outlet, where the housing includes an outlet coupler (e.g., outlet coupler 304) including a second component of the anti-rotation mechanism (e.g., second component 402 of anti-rotation mechanism 400) and a second component of the axial lock (e.g., second component 504 of axial lock 500). The method 2000 further includes aligning 2006 the first component of the anti-rotation mechanism with the second component of the anti-rotation mechanism, and inserting 2008 the outflow cannula into the housing outlet such that the first and second components of the anti-rotation mechanism engage one another prior to the first and second components of the axial lock. The anti-rotation mechanism limits rotation of the outflow cannula relative to the pump housing. The method 2000 further includes engaging 2010 the first component of the axial lock with the second component of the axial lock such that the axial lock inhibits axial movement of the outflow cannula relative to the pump housing.

Although certain steps of the example method are numbered, such numbering does not indicate that the steps must be performed in the order listed. Thus, particular steps need not be performed in the exact order they are presented, unless the description thereof specifically require such order. The steps may be performed in the order listed, or in another suitable order.

As described herein, the implantable blood pump assemblies of the present disclosure provide several advantages over previous VAD designs. For example, embodiments of the implantable blood pump assemblies disclosed herein include an outlet coupler and an outflow cannula that cooperatively form an anti-rotation mechanism and an axial lock. The respective components of the anti-rotation mechanism and the axial lock are positioned to permit assembly of the blood pump assembly in a certain order that reduces risk of the outflow cannula being subjected to excessive rotation or torsion during placement of the blood pump assembly and subsequent to placement of the blood pump assembly (i.e., post-operatively). For example, the components of the anti-rotation mechanism are configured to engage one another prior to the components of the axial lock, thereby ensuring that the components of the anti-rotation mechanism are engaged (and rotation thereby inhibited) prior to the axial lock being engaged. Further, in some embodiments, the anti-rotation mechanism permits connection of the outflow assembly and the outlet coupler in only a discrete number of orientations, thereby limiting the amount of rotation of the outflow cannula relative to the pump housing during assembly. Additionally, in some embodiments, the anti-rotation mechanism utilizes pre-existing structural features of outflow cannulas used for other purposes (e.g., spanner wrench grooves used for assembly of outflow cannula) to provide an anti-rotation function, thereby reducing the need for additional or extra components on the outflow cannula and reducing size and cost of the outflow cannula.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An implantable blood pump assembly comprising:
   a housing defining an inlet, an outlet, and a flow path extending from the inlet to the outlet, the housing comprising an outlet coupler;
   a rotor positioned within the flow path and operable to pump blood from the inlet to the outlet;
   a stator positioned within the housing and operable to drive the rotor; and
   an outflow cannula comprising a coupler assembly configured for removable mechanical connection to the outlet coupler, wherein the coupler assembly comprises a first component of an anti-rotation mechanism and a first component of an axial lock;
   wherein the outlet coupler comprises a second component of the anti-rotation mechanism and a second component of the axial lock;
   wherein the first and second components of the anti-rotation mechanism are positioned to engage one another and to inhibit rotation of the outlet coupler and the outflow cannula relative to one another prior to the first and second components of the axial lock engaging one another during insertion of the outflow cannula into the housing outlet.

2. The implantable blood pump assembly of claim 1, wherein the coupler assembly further comprises an annular seal, and wherein the outlet coupler includes a sealing surface that sealingly engages the seal during insertion of the outflow cannula into the housing outlet.

3. The implantable blood pump assembly of claim 2, wherein the seal is positioned such that the seal engages the sealing surface subsequent to the first and second components of the anti-rotation mechanism engaging one another.

4. The implantable blood pump assembly of claim 3, wherein the seal is positioned such that the seal engages the sealing surface prior to the first and second components of the axial lock engaging one another.

5. The implantable blood pump assembly of claim 3, wherein the seal is positioned such that the seal engages the sealing surface subsequent to the first and second components of the axial lock engaging one another.

6. The implantable blood pump assembly of claim 1, wherein the second component of the anti-rotation mechanism comprises a plurality of longitudinally-extending splines located on a radial inner surface of the outlet coupler, wherein the plurality of splines are spaced circumferentially about the radial inner surface of the outlet coupler.

7. The implantable blood pump assembly of claim 6, wherein the first component of the anti-rotation mechanism comprises a plurality of longitudinally-extending grooves defined in a radial outer surface of a sleeve of the coupler assembly, wherein the plurality of grooves are spaced circumferentially about the radial outer surface of the sleeve at distances that correspond to the circumferential spacing of the plurality of splines.

8. The implantable blood pump assembly of claim 7, wherein the plurality of grooves are spanner nut grooves configured for engagement with a spanner wrench.

9. The implantable blood pump assembly of claim 1, wherein the first and second components of the anti-rotation mechanism are arranged relative to one another such that the outflow cannula is selectively coupleable to the outlet coupler in one of a discrete number of orientations.

10. The implantable blood pump assembly of claim 9, wherein the discrete number of orientations is at least 4.

11. The implantable blood pump assembly of claim 1, wherein the first and second components of the anti-rotation mechanism, after engagement, permit limited rotation of the outflow cannula relative to the outlet coupler.

12. The implantable blood pump assembly of claim 1, wherein the first and second components of the axial lock comprise complementary threads.

13. The implantable blood pump assembly of claim 1, wherein the first and second components of the anti-rotation mechanism inhibit engagement of the first and second components of the axial lock when the first and second components of the anti-rotation mechanism are axially out of alignment.

14. The implantable blood pump assembly of claim 1, wherein the outflow cannula has an inflow end and an outflow end and comprises a flexible fluid conduit extending between the inflow end and the outflow end, wherein the coupler assembly is coupled to the fluid conduit at the inflow end of the outflow cannula.

15. The implantable blood pump assembly of claim 1, wherein the coupler assembly comprises:
   an adapter sleeve having a first end sized to be received within the housing outlet and a second end disposed within a fluid conduit of the outflow cannula, wherein the first end of the adapter sleeve includes the first component of the anti-rotation mechanism; and
   a screw ring rotatably coupled to the adapter sleeve and comprising the first component of the axial lock.

16. An implantable blood pump assembly comprising:
   a housing defining an inlet, an outlet, and a flow path extending from the inlet to the outlet, the housing comprising an outlet coupler;
   a rotor positioned within the flow path and operable to pump blood from the inlet to the outlet;
   a stator positioned within the housing and operable to drive the rotor; and
   an outflow cannula comprising a coupler assembly configured for removable mechanical connection to the outlet coupler, wherein the coupler assembly comprises:
      an adapter sleeve comprising one of: (i) a plurality of longitudinally-extending grooves or (ii) a plurality of longitudinally-extending splines; and
      a screw ring rotatably coupled to the adapter sleeve and comprising first threads;
   wherein the outlet coupler comprises:
      the other of (i) the plurality of longitudinally-extending grooves or (ii) the plurality of longitudinally-extending splines; and
      second threads configured to threadably engage the first threads,
   wherein the plurality of splines are configured for mating engagement with the plurality of grooves to inhibit relative rotation of the outflow cannula and the pump housing, and
   wherein the plurality of grooves and the plurality of splines are positioned to engage one another and to inhibit rotation of the outlet coupler and the outflow cannula relative to one another prior to the first and second threads engaging one another during insertion of the outflow cannula into the housing outlet.

17. The implantable blood pump assembly of claim 16, wherein the plurality of grooves and the plurality of splines inhibit engagement of the first and second threads when the plurality of grooves and the plurality of splines are axially out of alignment.

18. The implantable blood pump assembly of claim 16, wherein the plurality of grooves and the plurality of splines are arranged relative to one another such that the outflow cannula is selectively coupleable to the outlet coupler in one of a discrete number of orientations.

19. The implantable blood pump assembly of claim 16, wherein the plurality of grooves are spanner nut grooves configured for engagement with a spanner wrench.

20. A method of assembling an implantable blood pump, the method comprising:
 providing an outflow cannula including a coupler assembly that includes a first component of an anti-rotation mechanism and a first component of an axial lock;
 providing a blood pump including a housing defining an inlet, an outlet, and a flow path extending from the inlet to the outlet, wherein the housing includes an outlet coupler including a second component of the anti-rotation mechanism and a second component of the axial lock;
 aligning the first component of the anti-rotation mechanism with the second component of the anti-rotation mechanism;
 inserting the outflow cannula into the housing outlet such that the first and second components of the anti-rotation mechanism engage one another and inhibit rotation of the outlet coupler and the outflow cannula relative to one another prior to the first and second components of the axial lock engaging one another, wherein the anti-rotation mechanism limits rotation of the outflow cannula relative to the pump housing; and
 engaging the first component of the axial lock with the second component of the axial lock such that the axial lock inhibits axial movement of the outflow cannula relative to the pump housing.

\* \* \* \* \*